US012630795B2

(12) United States Patent
Kuno et al.

(10) Patent No.: US 12,630,795 B2
(45) Date of Patent: *May 19, 2026

(54) CELL CULTURE SUBSTRATE, METHOD FOR PRODUCING CELL CULTURE SUBSTRATE, AND METHOD FOR PRODUCING SPHEROIDS

(71) Applicant: TOSOH CORPORATION, Yamaguchi (JP)

(72) Inventors: Goshi Kuno, Mie (JP); Yu Imaizumi, Mie (JP)

(73) Assignee: TOSOH CORPORATION, Yamaguchi (JP)

( * ) Notice: Subject to any disclaimer, the term of this patent is extended or adjusted under 35 U.S.C. 154(b) by 905 days.

This patent is subject to a terminal disclaimer.

(21) Appl. No.: 17/284,976

(22) PCT Filed: Oct. 15, 2019

(86) PCT No.: PCT/JP2019/040502
§ 371 (c)(1),
(2) Date: Apr. 13, 2021

(87) PCT Pub. No.: WO2020/080364
PCT Pub. Date: Apr. 23, 2020

(65) Prior Publication Data
US 2021/0355424 A1     Nov. 18, 2021

(30) Foreign Application Priority Data
Oct. 16, 2018     (JP) ................................. 2018-194841

(51) Int. Cl.
| | |
|---|---|
| *C12M 1/12* | (2006.01) |
| *C12M 1/00* | (2006.01) |
| *C12N 11/08* | (2020.01) |

(52) U.S. Cl.
CPC ............ *C12M 25/14* (2013.01); *C12M 23/20* (2013.01); *C12N 11/08* (2013.01); *C12N 2539/10* (2013.01)

(58) Field of Classification Search
CPC ...... C12M 23/20; C12M 25/02; C12M 25/14; C12N 11/08
See application file for complete search history.

(56) References Cited

U.S. PATENT DOCUMENTS

| | | | | |
|---|---|---|---|---|
| 10,335,514 B2 * | 7/2019 | Iwazawa | .............. | C12N 5/0676 |
| 11,046,803 B2 * | 6/2021 | Maejima | .................. | C12M 3/00 |
| 11,441,120 B2 * | 9/2022 | Nakaguma | ............ | C08F 220/12 |
| 2010/0216242 A1 | 8/2010 | Shimizu et al. | | |
| 2017/0203005 A1 | 7/2017 | Iwazawa et al. | | |
| 2017/0342377 A1 | 11/2017 | Imaizumi et al. | | |
| 2021/0395688 A1 * | 12/2021 | Nakayama | ........... | C12N 5/0655 |
| 2023/0332102 A1 * | 10/2023 | Kadota | ................ | C12N 5/0618 |
| 2023/0416690 A1 * | 12/2023 | Kuno | ................... | C12N 5/0663 |
| 2024/0218322 A1 * | 7/2024 | Imaizumi | ............. | C12N 5/0068 |

FOREIGN PATENT DOCUMENTS

| | | | | |
|---|---|---|---|---|
| EP | 3 235 899 A1 | 10/2017 | | |
| EP | 3 315 596 A1 | 5/2018 | | |
| JP | 4-278075 A | 10/1992 | | |
| JP | 5-276938 A | 10/1993 | | |
| JP | H05276938 A | * 10/1993 | | |
| JP | 8-140673 A | 6/1996 | | |
| JP | 2008-278769 A | 11/2008 | | |
| JP | 2010-220605 A | 10/2010 | | |
| JP | 2013-099272 A | 5/2013 | | |
| JP | 2015-073520 A | 4/2015 | | |
| JP | 2016194054 A | * 11/2016 | | |
| JP | 6123247 B2 | * 5/2017 | | |
| JP | 6229503 B2 | * 11/2017 | | |
| JP | 2017212972 A | * 12/2017 | ........... | C12N 5/0068 |
| JP | 6314458 B2 | * 4/2018 | | |
| JP | 6497677 B2 | * 4/2019 | | |
| JP | 679332 | 11/2020 | | |
| WO | 2015/048136 A1 | 4/2015 | | |
| WO | 2016/052504 A1 | 4/2016 | | |
| WO | 2016/159153 A1 | 10/2016 | | |
| WO | 2016/208777 A1 | 12/2016 | | |
| WO | 2017/131241 A1 | 8/2017 | | |
| WO | WO-2018074432 A1 | * 4/2018 | ............. | C12M 3/00 |
| WO | 2018/116904 A1 | 6/2018 | | |

OTHER PUBLICATIONS

Yamazaki M, Tsuchida M, Kobayashi KY, Takezawa T, Mori Y. A novel method to prepare size-regulated spheroids composed of human dermal fibroblasts. Biotechnol Bioeng. Jun. 5, 1994;44(1):38-44. doi: 10.1002/bit.260440107. PMID: 18618444. (Year: 1994).*
RSC Adv. Mar. 7, 2022;12(12):7446-7452. doi: 10.1039/d2ra00493c. eCollection Mar. 1, 2022 (Year: 2022).*
Yamazaki et al. (Biotechnol Bioeng. 1994 38-44, referenced in IDS submitted Jul. 13, 2021) (Year: 1994).*
Hickey et al. (Front Bioeng Biotechnol. Mar. 22, 2019:7:45. doi: 10.3389/fbioe.2019.00045. eCollection 2019.) (Year: 2019).*
Yamazaki, M. et al., "A Novel Method to Prepare Size-Regulated Spheroids Composed of Human Dermal Fibroblasts", Biotechnology and Bioengineering, vol. 44, 1994, pp. 38-44.

(Continued)

*Primary Examiner* — Fereydoun G Sajjadi
*Assistant Examiner* — Joel D Levin
(74) *Attorney, Agent, or Firm* — GREENBLUM & BERNSTEIN, P.L.C.

(57) ABSTRACT

There are provided a cell culture substrate that enables efficient spheroid formation for cells and can form spheroids having a uniform size and an arbitrary shape at a high cell viability, a method for producing the cell culture substrate, and a method of producing spheroids in which the cell culture substrate is used and a cell viability inside of the spheroids is excellent. A cell culture substrate includes a substrate and a stimulus-responsive polymer coated on the substrate, wherein the stimulus-responsive polymer is a block copolymer having a water-insoluble block segment and a stimulus-responsive block segment, and the cell culture substrate includes the following two regions (A) and (B): (A) an island-shaped region having cell proliferation properties and stimulus responsiveness and having an area of 0.001 to 5 mm$^2$; and (B) a region adjacent to the region (A) and having no cell proliferation properties.

11 Claims, 13 Drawing Sheets

(56)                 References Cited

OTHER PUBLICATIONS

International Search Report issued in International Patent Application No. PCT/JP2019/040502, dated Dec. 3, 2019, along with English Translation thereof.
Written Opinion of the International Searching Authority issued in International Patent Application No. PCT/JP2019/040502, dated Dec. 3, 2019, along with English Translation thereof.
Extended European Search Report issued in European Patent Application No. 19873568.0 dated Jun. 20, 2022.

* cited by examiner

500μm

CELL CULTURE SUBSTRATE, METHOD FOR PRODUCING CELL CULTURE SUBSTRATE, AND METHOD FOR PRODUCING SPHEROIDS

TECHNICAL FIELD

The present invention relates to a cell culture substrate that enables efficient spheroid formation and can form spheroids having a uniform size and an arbitrary shape, a method for producing the cell culture substrate, and a method for producing spheroids using the cell culture substrate.

BACKGROUND ART

Pluripotent stem cells such as embryonic cells (ES cells) and artificial cells (iPS cells) are cells that have an ability to differentiate into various tissues of living bodies (pluripotency), and have received a great deal of attention as a cell source for the fields of regenerative medicine and drug discovery screening. In order to apply pluripotent stem cells to regenerative medicine and drug discovery screening, it is necessary to differentiate pluripotent stem cells into desired cells, and in this case, it is necessary to form spheroids (embryoid bodies) of pluripotent stem cells. In addition, pluripotent stem cells can differentiate into various cells, it is known that the optimal spheroid size differs depending on the type of cells after differentiation, and it is desirable to control the size and produce spheroids with a more uniform size.

In the related art, as a method of forming spheroids, a method of spontaneously forming aggregates with pluripotent stem cells using a substrate to which pluripotent stem cells do not adhere is known (for example, refer to Patent Literature 1). Although this method is excellent in mass productivity of spheroids, there is a problem of spheroids having a uniform size not being obtained.

As a method of forming spheroids having uniform size, a method of using a cell culture substrate having fine irregularities on the surface is known (for example, refer to Patent Literature 2). However, the cell culture substrate with such fine irregularities has problems that it is poor in mass production and it is not suitable for use in forming a large amount of spheroids. In addition, there is a problem that the shape of spheroids that can be formed is limited to a spherical shape, and spheroids having a shape other than a spherical shape cannot be formed.

CITATION LIST

Patent Literature

[Patent Literature 1] Japanese Unexamined Patent Publication No. H8-140673
[Patent Literature 2] Japanese Unexamined Patent Publication No. 2015-073520

SUMMARY OF INVENTION

Technical Problem

An object of the present invention is to provide a cell culture substrate that enables efficient spheroid formation for cells and can form spheroids having a uniform size and an arbitrary shape, a method for producing the cell culture substrate, and a method for producing spheroids using the cell culture substrate.

Solution to Problem

The inventors conducted extensive studies in view of the above points and as a result, found that the above problems can be solved by a substrate having a region having specific stimulus responsiveness formed thereon, and completed the present invention.

Specifically, the present invention provides the following [1] to [12].

[1] A cell culture substrate comprising a substrate and a stimulus-responsive polymer coated on the substrate,
wherein the stimulus-responsive polymer is a block copolymer having a water-insoluble block segment and a stimulus-responsive block segment, and the cell culture substrate includes the following two regions (A) and (B):
(A) an island-shaped region having cell proliferation properties and stimulus responsiveness and having an area of 0.001 to 5 mm$^2$; and
(B) a region adjacent to the region (A) and having no cell proliferation properties.
[2] The cell culture substrate according to [1], wherein the region (A) is composed of the following two regions (A1) and (A2), and the region (B) is composed of the following two regions (B1) and (B2):
(A1) cell proliferative region
(A2) stimulus-responsive region
(B1) substrate adhesion region
(B2) stimulus-responsive region
[3] The cell culture substrate according to [1] or [2], wherein the region (A) is formed by dispersing a temperature-responsive region having a diameter of 10 to 500 nm in the cell proliferative region or formed by dispersing a cell proliferative region having a diameter of 10 to 500 nm in a temperature-responsive region having no cell proliferation properties.
[4] The cell culture substrate according to any one of [1] to [3], comprising a substrate having two regions including a cell proliferative region and a region having no cell proliferation properties, and a layer containing a stimulus-responsive polymer formed on the substrate, wherein the ratio of the average roughness/layer thickness of the layer is 0.5 or more and 1 or less.
[5] The cell culture substrate according to [4], wherein the stimulus-responsive polymer is a block copolymer having a water-insoluble block segment and a stimulus-responsive block segment exceeding 90 wt %.
[6] The cell culture substrate according to any one of [1] to [5], wherein the region (A) is a plasma treatment region.
[7] The cell culture substrate according to any one of [1] to [6], wherein the cell culture substrate is used for spheroid formation for pluripotent stem cells.
[8] A method for producing the cell culture substrate according to any one of [1] to [7], comprising the following processes (1) and (2):
(1) a process of forming an island-shaped region having cell proliferation properties and an area of 0.001 to 5 mm$^2$ on a surface of a substrate having no cell proliferation properties; and
(2) a process of forming a layer of a stimulus-responsive substance on the surface of the substrate.
[9] The method for producing the cell culture substrate according to [8], wherein, in the process (1), on the surface of the substrate having no cell proliferation properties, a region having cell proliferation properties is formed by any of a plasma treatment, a UV treatment, and a corona treatment or a combination of a plurality thereof.

[10] The method for producing the cell culture substrate according to [8] or [9], wherein the substrate used in the process (1) has cell adhesion properties but has no cell proliferation properties.

[11] The method for producing the cell culture substrate according to [9] or [10], wherein the process (1) comprises a process of attaching a surface protective film having holes with an area of 0.001 to 10 mm$^2$ to the substrate.

[12] A method for producing spheroids, comprising the following processes (i) to (iii):

(i) a process of seeding a cell on the cell culture substrate according to any one of [1] to [8];

(ii) a process of culturing the seeded cell and forming a colony of cells adhered to the cell culture substrate; and (iii) a process of separating at least a part of the colony from the cell culture substrate by applying an external stimulus and forming a cell spheroid.

Advantageous Effects of Invention

According to the present invention, it is possible to provide a cell culture substrate that enables efficient spheroid formation for cells and can form spheroids having a uniform size and an arbitrary shape at a high cell viability, a method for producing the cell culture substrate, and a method of producing spheroids in which the cell culture substrate is used and a cell viability inside spheroids is excellent.

DESCRIPTION OF EMBODIMENTS

Figure 1:
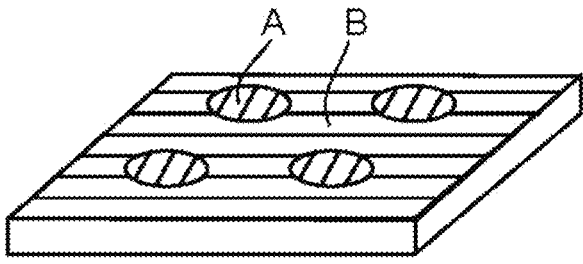
FIG. 1 is a schematic view (perspective view) of a cell culture substrate of the present invention.

Hereinafter, a form for implementing the present invention (hereinafter simply referred to as "the present embodiment") will be described in detail. The following present embodiment is only an example for describing the present invention, and the present invention is not limited to the following content. The present invention can be appropriately modified and implemented within the spirit and scope of the invention.

In this specification, "spheroid" refers to a three-dimensional agglomerate of cells formed by aggregating a plurality of cells, excluding sheet-like cells formed when cells are adhered to a substrate. Those having a spherical shape are preferable, and a spherical shape or a hollow shape having gaps formed by folding sheet-like cells may be used. In addition, in this specification, "colony" refers to a cell-sheet-like cell mass formed when cells adhere to a substrate.

In addition, in this specification, "stimulus responsiveness" means that the structure is changed or the degree of hydrophilicity/hydrophobicity is changed according to an external stimulus. Here, in this specification, "external stimulus" refers to a mechanical stimulus such as ultrasonic waves, vibration, and convection, an electromagnetic stimulus such as light, electricity, and magnetism, and a thermodynamic stimulus such as heating and cooling, except for a stimulus caused by a biological reaction such as an enzymatic reaction.

In addition, in this specification, "temperature responsiveness" means that the degree of hydrophilicity/hydrophobicity is changed when the temperature changes. Further, the boundary temperature at which the degree of hydrophilicity/hydrophobicity changes is referred to as a "response temperature."

In addition, in this specification, "organism-derived substance" is a substance present in the body of an organism, and may be a natural substance or a substance artificially synthesized by a gene modification technology or the like, or may be a substance chemically synthesized based on the organism-derived substance. The organism-derived substance is not particularly limited, and may be, for example, nucleic acids, proteins, and polysaccharides which are basic materials constituting living bodies, nucleotides, nucleosides, amino acids, or various sugars which are constituents thereof, or lipids, vitamins, or hormones.

In addition, in this specification, "cell adhesion" means ease of adhesion to a cell culture substrate at a culture temperature, and "having cell adhesion" means that cells can adhere to a substrate or a cell culture substrate directly or via an organism-derived substance at a culture temperature. In addition, "having no cell adhesion" means that cells cannot adhere to a substrate or a cell culture substrate at a culture temperature.

In addition, in this specification, "cell proliferation properties" refers to ease of cell proliferation at a culture temperature, and "having cell proliferation properties" means that cells adhere to a substrate or a cell culture substrate directly or via an organism-derived substance at a culture temperature, and can additionally proliferate. In addition, "having no cell proliferation properties" means that cells cannot adhere to a substrate or a cell culture substrate at a culture temperature or can adhere thereto but cannot proliferate. Further, "high cell proliferation properties" means that cells proliferate into more cells when compared in the same culture period.

A cell culture substrate according to an aspect of the present invention has the following two regions (A) and (B).

(A) An island-shaped region having cell proliferation properties and stimulus responsiveness and having an area of 0.001 to 5 mm$^2$.

(B) A region adjacent to the region (A) and having no cell proliferation properties.

The region (A) has cell proliferation properties and stimulus responsiveness. When the region has cell proliferation properties and stimulus responsiveness, in the cell culture substrate of the present invention, cells are cultured to form colonies, the colonies are separated with an external stimulus, and thereby spheroids can be produced. When the region has no cell proliferation properties or stimulus responsiveness, it is not possible to form colonies by culturing cells, but it is not possible to produce spheroids because it is not possible to separate colonies with an external stimulus.

The stimulus responsiveness is not particularly limited as long as colonies can be separated with an external stimulus, and examples thereof include temperature responsiveness, photoresponsiveness, pH responsiveness, magnetic responsiveness, electric field responsiveness, and mechanical stimulus responsiveness, and any of temperature responsiveness, photoresponsiveness, pH responsiveness, and mechanical stimulus responsiveness, or a combination of a plurality thereof is preferable, any of temperature responsiveness, photoresponsiveness, and mechanical stimulus responsiveness or a combination of a plurality thereof is more preferable, any of temperature responsiveness and mechanical stimulus responsiveness or a combination of a plurality thereof is particularly preferable, and temperature responsiveness is most preferable.

The region (A) is an island-shaped region having an area of 0.001 to 5 mm². If an island-shaped region having an area of 0.001 to 5 mm² is provided, when cells are cultured, it is possible to form colonies having an optimal size and shape when spheroids are produced. In addition, the shape of the colony can be controlled according to the shape of the island-shaped region, and spheroids having a shape other than the spherical shape can be produced. If an area is less than 0.001 mm² or more than 5 mm², when cells are cultured, it is not possible to form colonies having an optimal size, the shape of the spheroid is distorted or it is not possible to produce spheroids. In addition, an area of 0.005 to 1 mm² is preferable, an area of 0.01 to 0.5 mm² is more preferable, an area of 0.015 to 0.25 mm² is particularly preferable, and an area of 0.02 to 0.2 mm² is most preferable so that it is suitable to form spheroids suitable for use such as induction of differentiation of pluripotent stem cells.

In addition, the standard deviation/average area of the area of the region (A) is preferably 80% or less, more preferably 50% or less, particularly preferably 20% or less, and most preferably 5% or less so that it is suitable to produce spheroids having a uniform size and shape.

In the present invention, "island shape" refers to an independent region arranged in a plane like an island structure existing in a sea/island structure (for example, a part indicated by a reference numeral A in FIG. 1). Since the region (A) has an island shape, in the cell culture substrate of the present invention, cells are cultured to form colonies, the colonies are separated with an external stimulus, and thereby spheroids can be produced. When the region (A) has a non-island shape, for example, when it has a striped structure or the like, colonies are likely to break during separation, and spheroids having a uniform size and shape cannot be produced. The island shape is not particularly limited, and can be appropriately set according to a desired shape of spheroids, and examples thereof may include a circle, an ellipse, a polygon, and a closed shape formed with irregular straight lines or curves. In addition, regarding the island shape, a circle, an ellipse, or a polygon is preferable, a circle, an ellipse, or a rectangle is more preferable, a circle, an ellipse, or a square is particularly preferable, and a circle or an ellipse is most preferable so that it is suitable to produce spheroids having a shape close to a sphere.

In addition, in the present invention, the aspect ratio of the island shape is preferably 5 or less, more preferably 2 or less, particularly preferably 1.5 or less, and most preferably 1.1 or less so that it is suitable to produce spheroids having a shape close to a sphere. Here, in the present invention, the "aspect ratio" indicates a major diameter/minor diameter which is a ratio of the maximum diameter (major diameter) to the minimum diameter (minor diameter) of the shape.

The region (B) is adjacent to the region (A) and does not have cell proliferation properties. Since the region (B) is a region adjacent to the region (A) and having no cell proliferation properties, it is possible to form a state in which colonies are formed only in the region (A) and there are no colonies around the region (A) when cells are cultured, and it is possible to produce spheroids by separating colonies with an external stimulus. If the region (B) is not adjacent to the region (A) or has cell proliferation properties, since there are colonies around the region (A) when cells are cultured, when the colonies in the region (A) are separated with an external stimulus, the colonies in the region (A) are immobilized by the surrounding colonies so that spheroids cannot be produced, or the surrounding colonies adhere to the colonies in the region (A) so that spheroids having a uniform size and shape cannot be produced. In addition, it is preferable that the region (B) have neither cell proliferation properties nor have cell adhesion so that it is suitable to make the size and shape of the produced spheroids uniform.

The shape of the region (B) is not limited, except that it is adjacent to the region (A), and the region (B) is preferably adjacent to the length of 20% or more, more preferably 50% or more, and particularly preferably 80% or more of the boundary line with the region (A), and all the surrounding of the region (A) is most preferably the region (B) so that it is suitable to produce spheroids having a uniform size and shape. In addition, it is preferable to be a sea/island structure in which the region (A) has an island shape and the region (B) is a sea-like so that it is suitable to improve mass productivity of the cell culture substrate (for example, a part indicated by a reference numeral B in FIG. 1). Examples of regions other than the region (B) adjacent to the region (A) include a region having cell proliferation properties but having no stimulus responsiveness.

It is preferable that the region (B) also have stimulus responsiveness. When the region (B) has the same stimulus responsiveness as the region (A), it is not necessary to perform patterning with application of a stimulus-responsive substance in the region (A) and the region (B) when the cell culture substrate of the present invention is produced, and a stimulus-responsive substance may be uniformly coated on the entire surface of the cell culture substrate so that it is possible to improve mass productivity of the cell culture substrate. In addition, if a stimulus-responsive substance is coated on the region (B), this is preferable because it is possible to decrease cell adhesion in the region (B), it is easy to produce colonies having a uniform shape, and it is easy to produce spheroids having a uniform size and shape.

The area ratio between the region (A) and the region (B) is not particularly limited, and the area of the region (A) with respect to the entire substrate is preferably 10% or more, more preferably 30% or more, particularly preferably 50% or more, and most preferably 70% or more so that it is suitable to increase the amount of spheroids that can be produced per unit area of the culture substrate. In addition, the area of the region (B) with respect to the entire substrate is preferably 20% or more, more preferably 40% or more, particularly preferably 60% or more, and most preferably 80% or more so that it is suitable to provide a sufficient distance between the plurality of regions (A) and to prevent colonies in the plurality of regions (A) from fusing to form a non-uniform shape.

Figure 2:
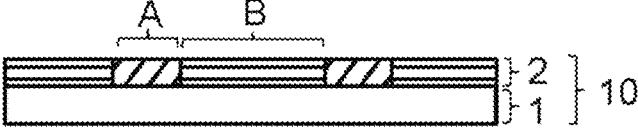
FIG. 2 is a schematic view (cross-sectional view) of a cell culture substrate having a layer of a stimulus-responsive polymer.
Figure 3:
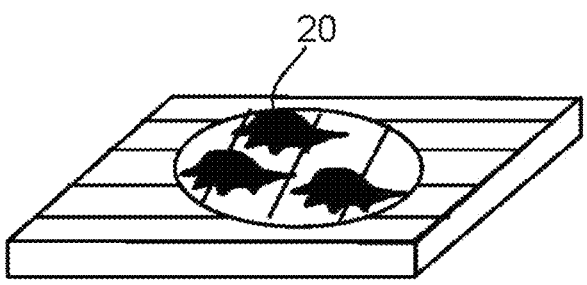
FIG. 3 is a schematic view showing a state of cells after a process (i) in a method of producing spheroids of the present invention.
Figure 4:
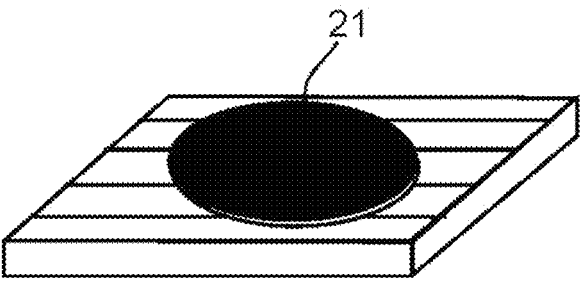
FIG. 4 is a schematic view showing a state of cells after a process (ii) in the method of producing spheroids of the present invention.
Figure 5:
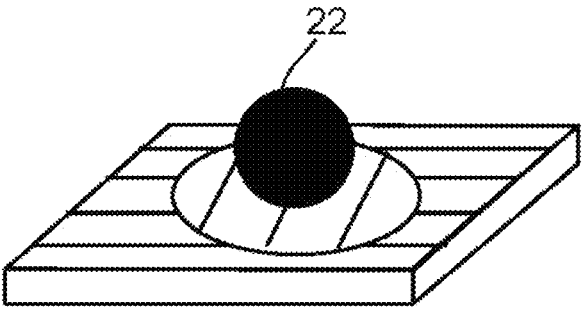
FIG. 5 is a schematic view showing a state of cells after a process (iii) in the method of producing spheroids of the present invention.
Figure 6:
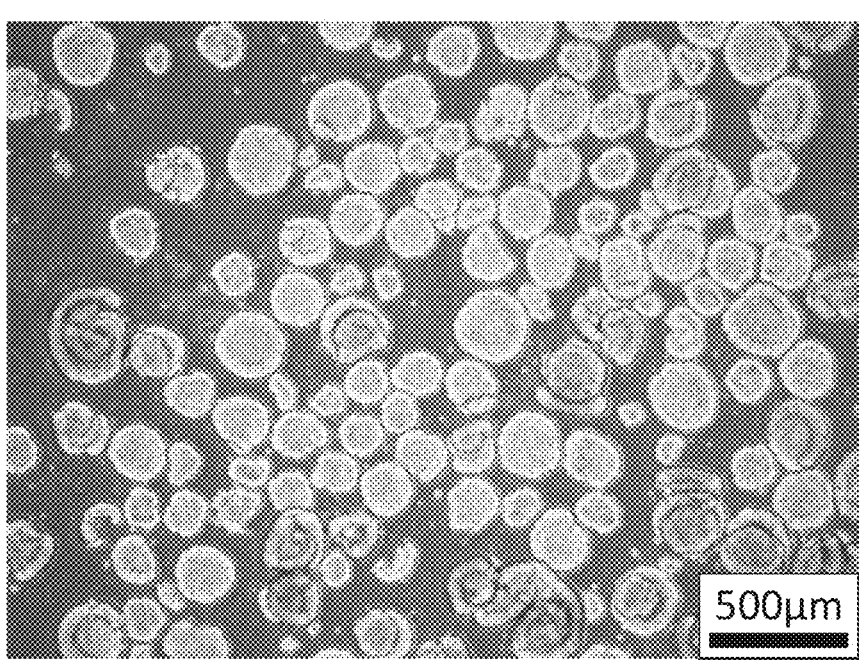
FIG. 6 is a phase-contrast microscopic image showing spheroids of Example 1.
Figure 7:
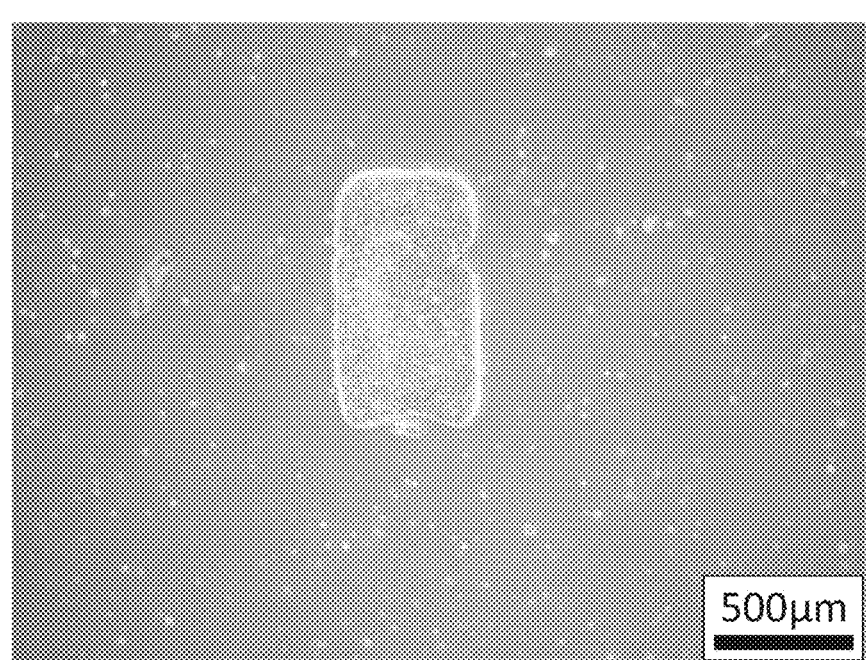
FIG. 7 is a phase-contrast microscopic image showing a colony of Example 2.
Figure 8:
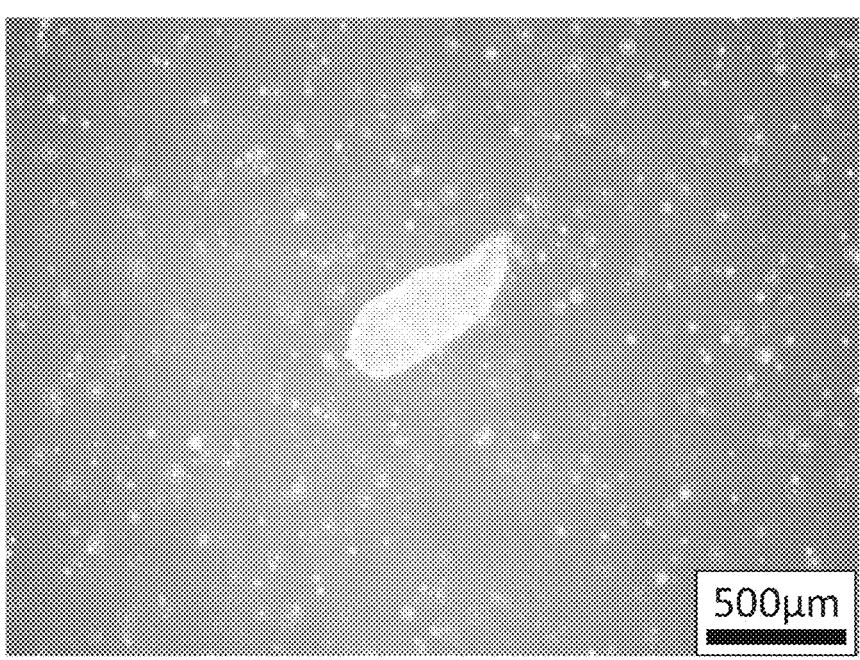
FIG. 8 is a phase-contrast microscopic image showing spheroids of Example 2.
Figure 9:
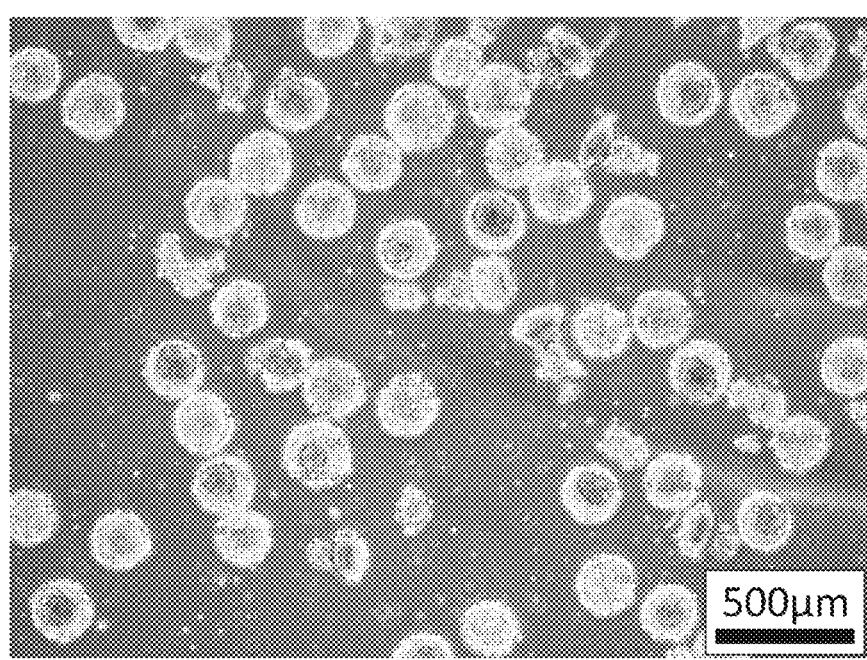
FIG. 9 is a phase-contrast microscopic image showing spheroids of Example 4.
Figure 10:
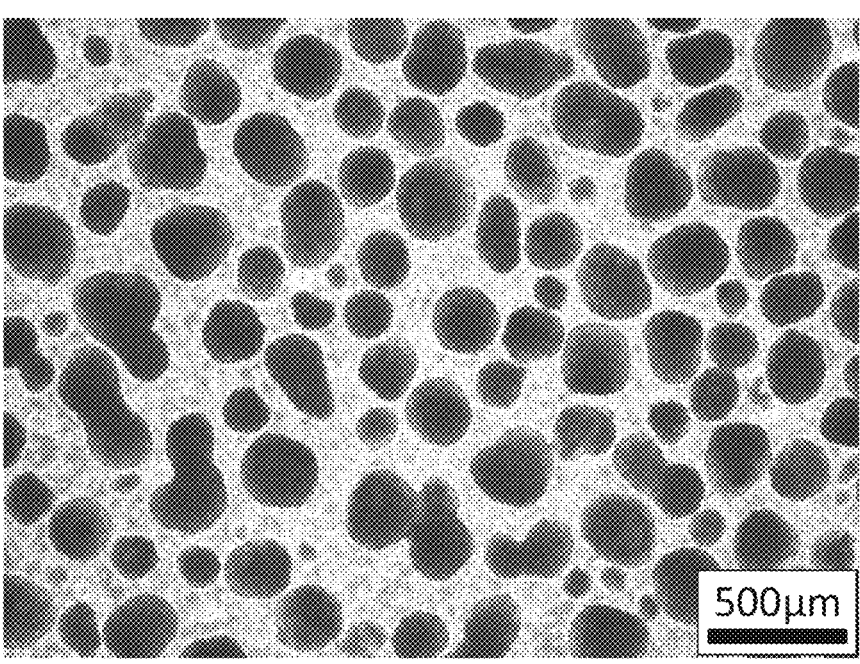
FIG. 10 is a phase-contrast microscopic image showing spheroids of Example 5.
Figure 11:
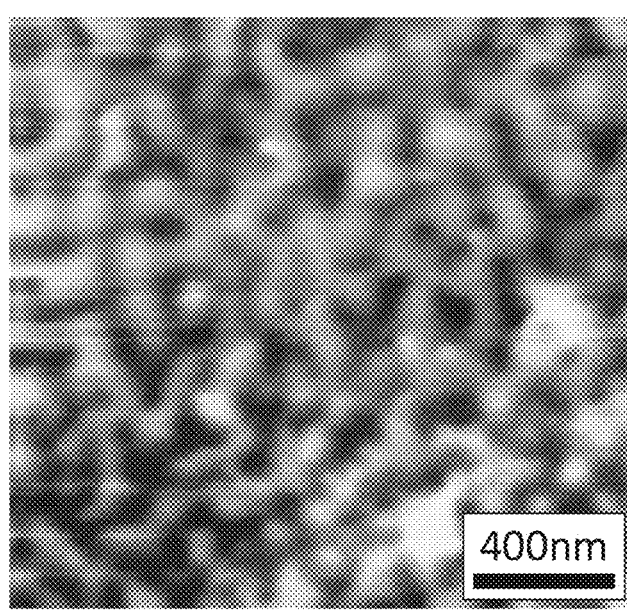
FIG. 11 is an atomic force microscopic image of a cell culture substrate of Example 7.
Figure 12:
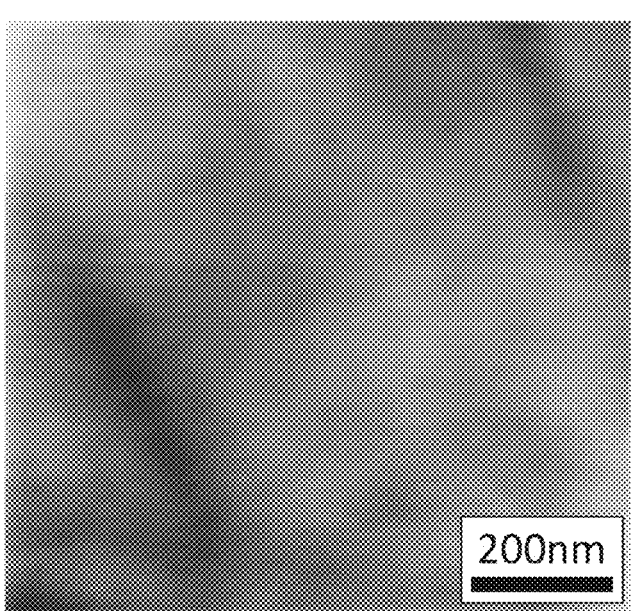
FIG. 12 is an atomic force microscopic image of a cell culture substrate of Example 8.
Figure 13:
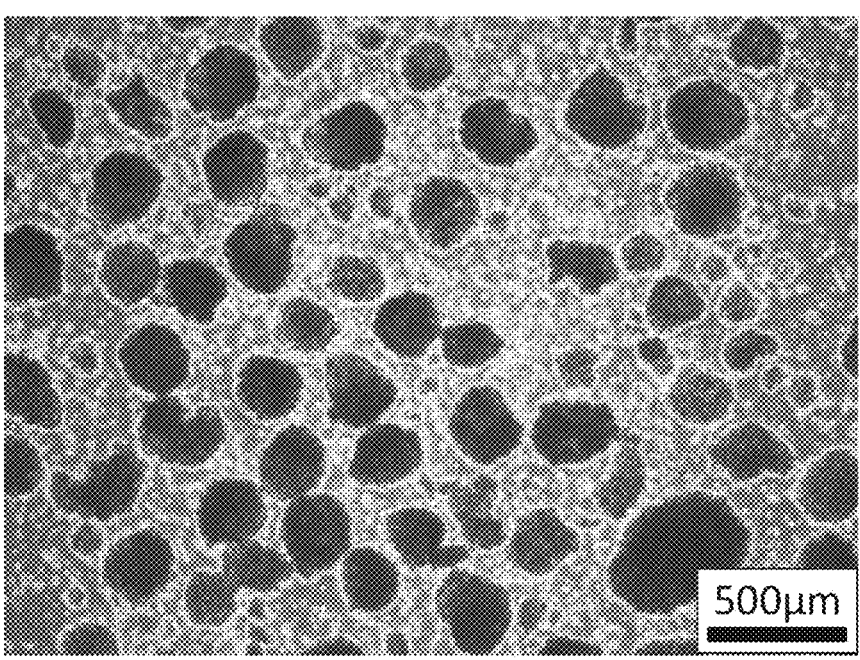
FIG. 13 is a phase-contrast microscopic image showing spheroids of Example 8.

In the present invention, it is preferable that stimulus responsiveness be due to a layer containing a stimulus-responsive polymer so that it is suitable to improve mass productivity of the cell culture substrate. Here, when the "substrate" is used in the present invention, it indicates a base substrate (for example, a part indicated by a reference numeral 1 in FIG. 2) in the article of the present invention. In addition, when the "cell culture substrate" is used, it indicates the entire article (for example, a part indicated by a reference numeral 10 in FIG. 2) for performing spheroid formation.

The type of the stimulus-responsive polymer is not particularly limited, and a block copolymer coated on the substrate, a copolymer immobilized on a substrate via a reactive group such as an azide group, a polymer immobilized on the substrate by applying monomers to the substrate and performing electron beam polymerization or radical polymerization on the substrate, or the like can be suitably used.

The stimulus-responsive polymer is preferably a temperature-responsive polymer so that it is suitable to produce spheroids without damaging cells by separating colonies with a weak stimulus. In addition, the response temperature is preferably 50° C. or lower and more preferably 35° C. or lower because cells can be cultured at a temperature close to the body temperature when cells are cultured on the cell culture substrate, and the response temperature is particularly preferably 25° C. or lower and most preferably 15° C. or lower so that it is suitable to prevent cells from being separated when an operation such as replacement of a culture medium is performed during culturing. In addition, the response temperature is preferably 0° C. or higher, more preferably 5° C. or higher, particularly preferably 10° C. or higher, and most preferably 15° C. or higher so that it is possible to form spheroids by performing a cooling operation at a temperature at which cells are not damaged.

The type of the temperature-responsive polymer is not particularly limited, and examples of monomer units include (meth)acrylamide compounds such as acrylamide and methacrylamide; N-alkyl-substituted (meth)acrylamide derivatives such as N,N-diethylacrylamide, N-ethylacrylamide, N-n-propylacrylamide, N-n-propylmethacrylamide, N-isopropylacrylamide, N-isopropylmethacrylamide, N-cyclopropylacrylamide, N-cyclopropylmethacrylamide, N-t-butylacrylamide, N-ethoxyethylacrylamide, N-ethoxyethylmethacrylamide, N-tetrahydrofurfurylacrylamide, and N-tetrahydrofurfurylmethacrylamide; N,N-dialkyl substituted (meth)acrylamide derivatives such as N,N-dimethyl (meth)acrylamide, N,N-ethylmethylacrylamide, and N,N-diethylacrylamide; (meth)acrylamide derivatives having a cyclic group such as 1-(1-oxo-2-propenyl)-pyrrolidine, 1-(1-oxo-2-propenyl)-piperidine, 4-(1-oxo-2-propenyl)-morpholine, 1-(1-oxo-2-methyl-2-propenyl)-pyrrolidine, 1-(1-oxo-2-methyl-2-propenyl)-piperidine, and 4-(1-oxo-2-methyl-2-propenyl)-morpholine; vinyl ethers such as methyl vinyl ether; and proline derivatives such as N-proline methyl ester acrylamide, and N,N-diethylacrylamide, N-n-propyl acrylamide, N-isopropylacrylamide, N-n-propylmethacrylamide, N-ethoxyethyl acrylamide, N-tetrahydrofurfurylacrylamide, and N-tetrahydrofurfurylmethacrylamide are preferable, N-n-propyl acrylamide and N-isopropylacrylamide are more preferable, and N-isopropylacrylamide is particularly preferable so that it is suitable for setting the response temperature to 0 to 50° C. In addition, if a culture medium at room temperature is used when replacing the culture medium in the culture operation, N-n-propyl acrylamide and N-proline methyl ester acrylamide are preferable so that it is suitable for setting the response temperature of the block copolymer to a temperature lower than room temperature.

In addition, the temperature-responsive polymer may be a copolymer, and examples thereof include a copolymer composed of at least two or more types of monomer units selected from among the above monomer units, and in particular, a copolymer of N-isopropylacrylamide and N-t-butyl acrylamide is preferable because the content of N-t-butyl acrylamide is changed so that it is within a range of 5 to 60 mol % and thus the response temperature can be controlled so that it is within a range of 5 to 30° C. In addition, a copolymer of monomer units constituting the above temperature-responsive segment and other monomer units may be used, and for example, when a copolymer with a hydrophilic monomer unit is used, the response temperature can be shifted to the high temperature side, and when a copolymer with a hydrophobic monomer unit is used, the response temperature can be shifted to the low temperature side. Here, the copolymer sequence may be any of a random sequence, an alternating sequence, and a block sequence.

In the present invention, the ratio of temperature-responsive constituent units contained in the temperature-responsive polymer is preferably 70 wt % or more, more preferably 80 wt % or more, particularly preferably 90 wt % or more, and most preferably 92 wt % or more so that it is suitable for rapidly performing a process of forming spheroids from colonies.

Regarding the stimulus-responsive polymer, a block copolymer having a stimulus-responsive block segment and a water-insoluble block segment or a block copolymer having a stimulus-responsive block segment and a reactive segment is preferable. When the stimulus-responsive polymer is the block copolymer, it is possible to improve mass productivity of the cell culture substrate, and it is possible to prevent the stimulus-responsive polymer from being mixed into the produced spheroids. The stimulus-responsive block segment is not particularly limited, and examples thereof include a polymer composed of the above temperature-responsive monomer units. In addition, when the block copolymer contains a water-insoluble block segment or a reactive segment, it is possible to prevent the block copolymer from being mixed into a culture solution, and it is possible to culture cells without contamination so that it is suitably possible to prevent the stimulus-responsive polymer from being mixed into spheroids. Here, in this specification, a block segment having "water-insolubility" means that at least a part of a homopolymer composed of only monomer units constituting the block segment is insoluble in water. In addition, the "reactive segment" indicates that the block segment has a reactive group, and can be immobilized on the substrate with an external stimulus such as heat, pH change, or light emission.

Examples of monomer units constituting the water-insoluble block segment include n-butyl acrylate, n-butyl methacrylate, isobutyl acrylate, isobutyl methacrylate, t-butyl acrylate, t-butyl methacrylate, n-hexyl acrylate, n-hexyl methacrylate, n-octyl acrylate, n-octyl methacrylate, n-decyl acrylate, n-decyl methacrylate, n-dodecyl acrylate, n-dodecyl methacrylate, n-tetradecyl acrylate, and n-tetradecyl methacrylate. In addition, those having a reactive group are preferable because they are suitable for firmly immobilizing block copolymers to a substrate, and examples thereof include 4-azidophenyl acrylate, 4-azidophenyl methacrylate, 2-((4-azidobenzoyl)oxy)ethyl acrylate, and 2-((4-azidobenzoyl)oxy)ethyl methacrylate. In addition, structures having an aromatic ring are preferable because they are suitable for improving cell proliferation properties, and examples thereof include 2-hydroxyphenyl acrylate, 2-hydroxyphenyl methacrylate, 3-hydroxyphenyl acrylate, 3-hydroxyphenyl methacrylate, 4-hydroxyphenyl acrylate, 4-hydroxyphenyl methacrylate, N-(2-hydroxyphenyl)acrylamide, N-(2-hydroxyphenyl)methacrylamide, N-(3-hydroxyphenyl)acrylamide, N-(3-hydroxyphenyl)methacrylamide, N-(4-hydroxyphenyl)acrylamide, N-(4-hydroxyphenyl)methacrylamide, and styrene.

In the present invention, examples of monomer units constituting the reactive block segment include 4-azidophenyl acrylate, 4-azidophenyl methacrylate, 2-((4-azido-benzoyl)oxy)ethyl acrylate, and 2-((4-azidobenzoyl)oxy)ethyl methacrylate.

In the present invention, the water-insoluble block segment or the reactive block segment may also contain repeating units for controlling a response temperature of the block copolymer. Repeating units for controlling a response temperature of the block copolymer may include, for example, hydrophilic or hydrophobic components, and are not particularly limited, and examples thereof include those having an amino group such as 2-dimethylaminoethyl acrylate, 2-dimethylaminoethyl methacrylate, 2-diethylaminoethyl acrylate, 2-diethylaminoethyl methacrylate, and N-[3-(dimethylamino)propyl]acrylamide; those having betaine such as N-(3-sulfopropyl)-N-methacryloyloxyethyl-N,N-dimethyl-ammonium betaine, and N-methacryloyloxyethyl-N,N-dimethylammonium-α-N-methylcarboxy betaine; those having a polyethylene glycol group or a methoxyethyl group such as hydroxyethyl acrylate, hydroxyethyl methacrylate, N-(2-hydroxyethyl)acrylamide, polyethylene glycol monoacrylate, polyethylene glycol monomethacrylate, polypropylene glycol monoacrylate, polypropylene glycol monomethacrylate, methoxypolyethylene glycol monoacrylate, methoxypolyethylene glycol monomethacrylate, diethylene glycol monomethyl ether acrylate, diethylene glycol monomethyl ether methacrylate, diethylene glycol monoethyl ether acrylate, diethylene glycol monoethyl ether methacrylate, 2-methoxyethyl acrylate, 2-methoxyethyl methacrylate, 2-ethoxyethyl acrylate, 2-ethoxyethyl methacrylate, 3-butoxyethyl acrylate, 3-butoxyethyl methacrylate, 3-butoxy-ethylacrylamide, furfuryl acrylate, furfuryl methacrylate, tetrahydrofurfuryl acrylate, and tetrahydrofurfuryl methacrylate; those having an acrylate group such as methoxymethyl acrylate, methoxymethyl methacrylate, 2-ethoxymethyl acrylate, 2-ethoxymethyl methacrylate, 3-butoxymethyl acrylate, 3-butoxymethyl methacrylate, and 3-butoxymethylacrylamide; and those having a phosphorylcholine group such as 2-methacryloyloxyethylphosphorylcholine, 2-acryloyloxyethylphosphorylcholine, 3-(meth)acryloyloxypropylphosphorylcholine, 4-(meth)acryloyloxybutylphosphorylcholine, 6-(meth)acryloyloxyhexylphosphorylcholine, 10-(meth)acryloyloxydecylphosphorylcholine, ω-(meth)acryloyl(poly)oxyethylenephosphorylcholine, 2-acrylamide ethylphosphorylcholine, 3-acrylamide propylphosphorylcholine, 4-acrylamide butylphosphorylcholine, 6-acrylamide hexylphosphorylcholine, 10-acrylamide decylphosphorylcholine, and ω-(meth)acrylamide (poly) oxyethylene phosphorylcholine.

The water-insoluble block segment or the reactive block segment may be a copolymer, and a copolymer sequence may be any of a random sequence, an alternating sequence, and a block sequence.

The proportion of constituent units of the water-insoluble block segment or the reactive block segment is preferably 1 wt % or more, more preferably 2 wt % or more, particularly preferably 5 wt % or more, and most preferably 10 wt % or more so that it is suitable to prevent the block copolymer from being mixed into the culture solution and cells from being contaminated, and the undifferentiated maintenance rate in subculture is high.

The molecular weight of the stimulus-responsive polymer in the present invention is not particularly limited, and the number average molecular weight is preferably 1,000 to 1,000,000, more preferably 2,000 to 500,000, particularly preferably 5,000 to 300,000, and most preferably 10,000 to 200,000 so that it is suitable to increase the strength of the stimulus-responsive polymer.

In the present invention, the content of a component having a number average molecular weight of 5,000 or less contained in the stimulus-responsive polymer is preferably 50% or less, more preferably 30% or less, particularly preferably 10% or less, and most preferably 5% or less so that it is suitable to prevent the stimulus-responsive polymer from being mixed into spheroids. In addition, the content of a component having a number average molecular weight of 10,000 or less is preferably 50% or less, more preferably 30% or less, particularly preferably 10% or less, and most preferably 5% or less. In addition, the content of a component having a number average molecular weight of 30,000 or less is preferably 50% or less, more preferably 30% or less, particularly preferably 10% or less, and most preferably 5% or less. The content of components having a specific molecular weight or less contained in the block copolymer can be measured by gel permeation chromatography.

In the present invention, the amount of the stimulus-responsive polymer eluted in water is preferably 50% or less, more preferably 30% or less, particularly preferably 10% or less, and most preferably 5% or less so that it is suitable to prevent the stimulus-responsive polymer from being mixed into spheroids. The amount of the stimulus-responsive polymer eluted in water indicates a weight loss rate of the stimulus-responsive polymer before and after a substrate on which a layer of a stimulus-responsive polymer is formed is immersed in water at 25° C. for 1 hour. Here, the method of measuring the weight loss of the stimulus-responsive polymer is not particularly limited, and a method that is generally used can be used for measurement, and for example, an FT-IR method, and a method according to measurement of an average film thickness can be used.

The stimulus-responsive polymer in the present invention may contain, as necessary, a chain transfer agent, a polymerization initiator, a polymerization inhibitor, and the like. The chain transfer agent is not particularly limited, and those generally used can be suitably used, and examples thereof include dithiobenzoate, trithiocarbonate, 4-cyano-4-[(dodecylsulfonylthiocarbonyl)sulfonyl]pentanoic acid, 2-cyanopropan-2-yl N-methyl-N-(pyridin-4-yl)carbamodithioate, and methyl 2-methylpropionate(4-pyridinyl)carbamodithioate. In addition, the polymerization initiator is not particularly limited, and those generally used can be suitably used, and examples thereof include azobisisobutyronitrile, 1,1'-azobis(cyclohexanecarbonitrile), di-tert-butyl peroxide, tert-butyl hydroperoxide, hydrogen peroxide, potassium peroxydisulfate, benzoyl peroxide, triethylborane, and diethylzinc. In addition, the polymerization inhibitor is not particularly limited, and those generally used can be suitably used, and examples thereof include hydroquinone, p-methoxyphenol, triphenyl-verdazyl, 2,2,6,6-tetramethylpiperidinyl-1-oxyl, and 4-hydroxy-2,2,6,6-tetramethylpiperidinyl-1-oxyl.

A method of synthesizing a stimulus-responsive polymer in the present invention is not particularly limited, and a living radical polymerization technique described in "Radical Polymerization Handbook," pp. 161 to 225 (2010) published by NTS can be used.

In the present invention, the layer thickness of the layer formed of a stimulus-responsive polymer is preferably 1,000 nm or less, more preferably 200 nm or less, particularly preferably 100 nm or less, and most preferably 50 nm or less so that it is suitable to improve cell proliferation properties. In addition, the layer thickness of the layer formed of a stimulus-responsive polymer is preferably 5 nm or more, more preferably 20 nm or more, particularly preferably 30 nm or more, and most preferably 35 nm or more so that it is suitable to rapidly perform a process of forming spheroids from colonies. Here, in the present invention, the "layer thickness" of the layer formed of a stimulus-responsive polymer indicates the length from the interface between the substrate and the layer formed of a stimulus-responsive polymer to the mountain part in the surface structure of the layer formed of a stimulus-responsive polymer in the out-of-plane direction. The layer thickness of the layer formed of a stimulus-responsive polymer can be calculated by, for a sample obtained by immersing a cell culture substrate in water at a culture temperature for 24 hours or longer and rapidly drying it by blowing air or the like, measuring a cross-sectional image under a transmission electron microscope using an ultra-thin section of the cell culture substrate prepared by a microtome in a range in which the layer thickness exceeds 10 nm, and measuring and averaging the distances of 10 randomly selected points. In addition, the layer thickness can be measured using an ellipsometer in a range of 10 nm or less.

In the present invention, the ratio of the average roughness/layer thickness of the surface of the layer formed of a stimulus-responsive polymer is preferably 0.3 or more so that it is suitable to improve cell proliferation properties and additionally to rapidly perform a process of forming spheroids from colonies. When the ratio of average roughness/layer thickness of the surface of the stimulus-responsive polymer is 0.3 or more, it is possible to provide a region in which cells strongly adhere and a region in which cells do not strongly adhere, and it is possible to improve cell proliferation properties and rapidly perform a process of forming spheroids from colonies. The ratio of the average roughness/layer thickness of the surface of the layer formed of a stimulus-responsive polymer is more preferably 0.5 or more, particularly preferably 0.7 or more, and most preferably 0.9 or more so that it is suitable to improve cell proliferation properties and additionally to rapidly perform a process of forming spheroids from colonies. Here, in the present invention, the "average roughness" of the surface of the layer formed of a stimulus-responsive polymer indicates the average height of the contour curve obtained according to JIS B 0601: 2013, and can be calculated by measuring an atomic force microscopic image of a typical surface of the cell culture substrate, and obtaining an average height at 10 randomly selected points in the roughness curve with 1 μm as a reference length, and similar to the above measurement of the layer thickness, measurement is performed using a sample obtained by immersing a cell culture substrate in water at a culture temperature for 24 hours or longer and rapidly drying it by blowing air or the like.

In the cell culture substrate according to an aspect of the present invention, it is preferable that the region (A) be composed of the following two regions (A1) and (A2), and the region (B) be composed of the following two regions (B1) and (B2).

(A1) cell proliferative region
(A2) stimulus-responsive region
(B1) substrate adhesion region
(B2) stimulus-responsive region Here, the "substrate adhesion region" refers to a region in which a component coated on a cell culture substrate adheres to the substrate. Since the stimulus-responsive region has an effect of deteriorating cell proliferation properties, when the region (A) is composed of two regions (A1) and (A2), it is possible to suitably perform spheroid formation for pluripotent stem cells, which are difficult to proliferate with adhering to the cell culture substrate, and separation from the cell culture substrate with a stimulus response. In addition, when the region (B) has (B1), it is suitable for firmly immobilizing a component coated on a cell culture substrate on the substrate. In addition, when the region (B) has the region (B2), it is suitable for preventing pluripotent stem cells from proliferating in the region (B) and for forming uniform spheroids. The regions (A1) and (A2), and the regions (B1) and (B2) can be confirmed by measuring an atomic force microscopic image or a transmission electron microscopic image of the surface of the cell culture substrate and determining main components present in respective regions. For example, when a copolymer composed of cell proliferative monomer units and stimulus-responsive monomer units is coated, the monomer units present in respective regions can be determined from the phase image in the atomic force microscopic image and the contrast in the transmission electron microscopic image.

The regions (A1) and (A2) and the regions (B1) and (B2) can be suitably formed by coating a block copolymer composed of a combination of monomer units having a largely different degree of hydrophilicity/hydrophobicity. However, the composition and application amount of the copolymer that can form the regions (A1) and (A2), and the regions (B1) and (B2) differ depending on the type of the block copolymer. When the block copolymer is a diblock compound of butyl methacrylate and N-isopropylacrylamide, a diblock compound in which one component exceeds 90% is preferable, a diblock compound in which N-isopropylacrylamide exceeds 90% is more preferable, a diblock compound in which N-isopropylacrylamide exceeds 92% is particularly preferable, and a diblock compound in which N-isopropylacrylamide exceeds 94% is most preferable. In addition, regarding application, a film thickness of 1 to 200 nm is preferable, a film thickness of 5 to 100 nm is more preferable, a film thickness of 10 to 50 nm is particularly preferable, and a film thickness of 15 to 35 nm is most preferable.

In the present invention, preferably, the region (A) is formed by dispersing a temperature-responsive region having a diameter of 10 to 500 nm in the cell proliferative region or formed by dispersing a cell proliferative region having a diameter of 10 to 500 nm in the temperature-responsive region having no cell proliferation properties. When the region (A) is formed by dispersing the region having a diameter of 10 to 500 nm, it is possible to suitably perform spheroid formation for pluripotent stem cells and separation from the cell culture substrate according to a stimulus response.

In the present invention, the region (A) is preferably a plasma treatment region so that it is suitable to improve mass productivity of spheroids and to form more uniform spheroids. When the region (A) is a plasma treatment region, many cells can be collected only in the region (A) and a large amount of uniform spheroids can be easily formed.

In the present invention, the difference between zeta potentials of the region (A) and the region (B) is preferably 5 mV or more, more preferably 10 mV or more, particularly preferably 20 mV or more, and most preferably 40 mV or more so that it is suitable to improve mass productivity of spheroids and form more uniform spheroids.

In the present invention, preferably, there is no partition wall around the region (A) through which cells cannot cross so that it is suitable to improve mass productivity of spheroids. When there is no partition wall around the region (A) through which cells cannot cross, since cells can move freely and many cells can be collected in the region (A), it is possible to improve mass productivity of spheroids. In addition, since it is suitable to improve mass productivity of spheroids, more preferably, there is no partition wall having a height of 1 μm or more, particularly preferably, there is no partition wall having a height of 0.1 μm or more, and most preferably, there is no partition wall having a height of 0.05 μm or more.

In the present invention, as necessary, the cell culture substrate may contain an organism-derived substance on its surface. The organism-derived substance is not particularly limited, and examples thereof include matrigel, laminin, fibronectin, vitronectin, and collagen.

These organism-derived substances may be natural substances or substances artificially synthesized by gene modification technology or the like, or may be fragments cut with a restriction enzyme or the like or synthetic proteins or synthetic peptides based on these organism-derived substances.

In the present invention, regarding the matrigel, commercial products, for example, Matrigel (commercially available from Corning Incorporated) and Geltrex (commercially available from Thermo Fisher Scientific), can be suitably used in consideration of availability.

The type of the laminin is not particularly limited, and for example, laminin 511, laminin 521 or laminin 511-E8 fragments which have been reported to exhibit high activity with respect to α6β1 integrin expressed on the surface of human iPS cells can be used. The laminin may be a natural substance or a substance artificially synthesized by gene modification technology or the like, or synthetic proteins or synthetic peptides based on the laminin. In consideration of availability, commercial products, for example, iMatrix-511 (commercially available from Nippi. Inc.), can be suitably used.

The vitronectin may be a natural substance or a substance artificially synthesized by gene modification technology or the like, or synthetic proteins or synthetic peptides based on the vitronectin. In consideration of availability, commercial products, for example, vitronectin, those derived from human plasma (commercially available from Wako Pure Chemical Industries, Ltd.), synthemax (commercially available from Corning Incorporated), and Vitronectin (VTN-N) (commercially available from Thermo Fisher Scientific), can be suitably used.

The fibronectin may be a natural substance or a substance artificially synthesized by a gene modification technology or the like, or synthetic proteins or synthetic peptides based on the fibronectin. In consideration of availability, commercial products, for example, a fibronectin solution, those derived from human plasma (commercially available from Wako Pure Chemical Industries, Ltd.), and Retronectin (commercially available from Takara Bio Inc.), can be suitably used.

The type of the collagen is not particularly limited, and for example, type I collagen and type IV collagen can be used. The collagen may be a natural substance or a substance artificially synthesized by a gene modification technology or the like, or synthetic peptides based on the collagen. In consideration of availability, commercial products, for example, collagen I, from human (commercially available from Corning Incorporated) and collagen IV, from human (commercially available from Corning Incorporated), can be suitably used.

In the present invention, the organism-derived substance is preferably immobilized on the cell culture substrate by a non-covalent bond rather than a covalent bond because it is possible to prevent denaturation of the organism-derived substance and it is possible to improve cell proliferation properties. Here, in the present invention, the "non-covalent bond" indicates a binding force other than a covalent bond derived from an intermolecular force such as an electrostatic interaction, a water-insoluble interaction, a hydrogen bond, a π-π interaction, a dipole-dipole interaction, a London dispersion force, and other Van der Waals interactions. Immobilization of the organism-derived substance on the block copolymer may be due to a single binding force or a combination of a plurality of binding forces.

In the present invention, the method of immobilizing an organism-derived substance is not particularly limited, but for example, a method of applying an organism-derived substance solution to a cell culture substrate for a predetermined time for immobilization, or a method of adding an organism-derived substance to a culture solution when cells are cultured and thus adsorbing the organism-derived substance to the cell culture substrate for immobilization can be suitably used.

In the present invention, the material of the substrate is not particularly limited, and not only substances such as glass and polystyrene generally used for cell culture but also substances that can generally impart forms, for example, polymer compounds such as polycarbonate, polyethylene terephthalate, polyvinylidene fluoride, polytetrafluoroethylene, polyethylene, polypropylene, and polymethylmethacrylate, ceramic, and metals can be used. In consideration of ease of a culture operation, the material of the substrate preferably contains at least one type of glass, polystyrene, polycarbonate, polyethylene terephthalate, polyethylene, and polypropylene, more preferably contains at least one type of glass, polystyrene, polycarbonate, polyethylene terephthalate, and polyethylene, and particularly preferably contains polystyrene, polycarbonate, polyethylene terephthalate, or polyethylene because it is suitable to increase the flexibility. In addition, polystyrene, polycarbonate or polyethylene terephthalate is most preferable because it is suitable to impart cell proliferation properties by patterning according to a hydrophilization treatment to be described below.

The shape of the substrate is not particularly limited, and may be a planar shape such as a plate or a film or may be a fiber, a porous particle, a porous membrane, or a hollow fiber. In addition, a container generally used for cell culture or the like (a cell culture disk such as a petri dish, a flask, a plate, etc.) may be used. In consideration of ease of a culture operation, a planar shape such as a plate or a film or a flat porous membrane is preferable. In addition, a structure for classifying spheroids may be provided by providing partition plates on the substrate as necessary.

In the present invention, preferably, the substrate is a porous substrate, and the pore diameter of the porous substrate is smaller than that of cells so that it is suitable to rapidly perform a process of forming spheroids from colonies, and further, even if large spheroids are produced, it is possible to uniformly distribute nutrition to the inside of the colonies. In addition, the pore diameter is preferably 0.01 to 8 μm, more preferably 0.01 to 3 μm, particularly preferably 0.01 to 1 μm, and most preferably 0.1 to 1 μm so that it is suitable to rapidly perform a process of forming spheroids from colonies. Here, in the present invention, the "pore diameter" of the porous substrate indicates an average value of diameters of pores of the porous substrate in the in-plane direction of the porous substrate and can be calculated by measuring diameters of 20 or more pores in a laser microscopic image, a scanning electron microscopic image, or a transmission electron microscopic image of the porous substrate and obtaining an average value.

The porosity of the porous substrate is preferably 0.01 to 60%, more preferably 0.01 to 20%, particularly preferably 0.01 to 4%, and most preferably 0.01 to 1.5% so that it is suitable to rapidly perform a process of forming spheroids from colonies. Here, in the present invention, the "porosity" of the porous substrate indicates a value obtained by dividing a total area of pore parts by a substrate area for one main surface of the surfaces of the porous substrate, and indicates the amount of voids present on the surface of the substrate in terms of area ratio, and this can be measured by observing a square region having one side with a length of 200 times or more the pore diameter of pores of the porous substrate in a laser microscopic image, a scanning electron microscopic image, or a transmission electron microscopic image of the porous substrate.

The cell culture substrate of the present invention may be sterilized. A sterilization method is not particularly limited, and high pressure steam sterilization, UV sterilization, γ-ray sterilization, ethylene oxide gas sterilization, or the like can be used. High pressure steam sterilization, UV sterilization, or ethylene oxide gas sterilization is preferable because it is suitable to prevent denaturation of the block copolymer, UV sterilization or ethylene oxide gas sterilization is more preferable because it is suitable to prevent deformation of the substrate, and ethylene oxide gas sterilization is particularly preferable because it is excellent in mass productivity.

Cells cultured using the cell culture substrate of the present invention are not particularly limited as long as they can adhere to the surface before a stimulus is applied according to a temperature drop. For example, in addition to various strained cells such as Chinese hamster ovary-derived CHO cells, mouse connective tissue L929, human fetal kidney-derived HEK293 cells, and human cervical cancer-derived HeLa cells, for example, epithelial cells and endothelial cells that constitute tissues and organs in living bodies, skeletal muscle cells showing contractility, smooth muscle cells, myocardial cells, neuron cells that constitute the nervous system, glia cells, fibroblasts, hepatocytes, hepatic nonparenchymal cells, and adipocytes involved in metabolism of living bodies, and as cells having a differentiation ability, stem cells present in various tissues such as mesenchymal stem cells, bone marrow cells, and Muse cells, and also, stem cells (pluripotent stem cells) having pluripotency such as ES cells and iPS cells, and cells induced to differentiate from them can be used. In consideration of cell proliferation properties and separation in the culture substrate of the present invention, stem cells or pluripotent stem cells are preferable, mesenchymal stem cells or pluripotent stem cells are more preferable, pluripotent stem cells are particularly preferable, and iPS cells are most preferable.

The present invention relates to a method of producing the cell culture substrate, which is excellent in mass productivity. The method includes the following processes (1) and (2).

(1) A process of forming an island-shaped region having cell proliferation properties and an area of 0.001 to 5 mm$^2$ on a surface of a substrate having no cell proliferation properties.

(2) A process of forming a layer of a stimulus-responsive substance on the surface of the substrate.

Hereinafter, the processes (1) to (2) in the method for producing a cell culture substrate of the present invention will be described in detail.

In the process (1) in the method for producing a cell culture substrate of the present invention, a substrate having no cell proliferation properties is used to form an island-shaped region having cell proliferation properties and an area of 0.001 to 5 mm$^2$ on the surface of the substrate. When a cell proliferative region is formed by patterning using a substrate having no cell proliferation properties, it is possible to efficiently produce a cell proliferative region having an arbitrary shape and size. Regarding a method of forming a cell proliferative region, since it is suitable to improve mass productivity of the cell culture substrate, a hydrophilization treatment such as a plasma treatment, a UV treatment, or a corona treatment or a method of coating a substance having cell proliferation properties to a substrate is preferable, a method of imparting cell proliferation properties to a part of a region on a substrate by a hydrophilization treatment such as a plasma treatment, a UV treatment, or a corona treatment is more preferable, and among these, a plasma treatment is particularly preferable.

The patterning method is not particularly limited, and examples thereof include a method in which, a hydrophilization treatment such as a plasma treatment, a UV treatment, or a corona treatment is performed in a state of that a substrate is covered with a metal mask, a silicon mask, a surface protective film, or the like, and thus the hydrophilization treatment is performed to form a desired shape, and a method of coating a substrate with a substance having cell proliferation properties in a desired shape by a photolithography method or an inkjet method. It is preferable to perform a hydrophilization treatment such as a plasma treatment, a UV treatment, or a corona treatment while a surface protective film in which laser-processed holes are formed is attached to a substrate because it is suitable to improve mass productivity of the cell culture substrate.

In addition, regarding a method of performing patterning by a method other than the process (1), a method of forming a region having no cell proliferation properties on the surface of the substrate having cell proliferation properties can be used. Regarding this method, for example, a method in which a substrate having cell proliferation properties is used or after cell proliferation properties are imparted to the entire surface of a substrate having no cell proliferation properties, a substance having no cell proliferation properties is coated on the substrate in a desired shape according to a photolithography method or an inkjet method can be used.

In the process (2) in the method for producing a cell culture substrate of the present invention, a layer of a stimulus-responsive substance is formed on the surface of the substrate. In this case, when a layer of a stimulus-responsive substance and having a layer thickness of 100 nm or less is formed on the surface of the substrate, also in the case of performing the process (2) after the process (1), molecular chains of the stimulus-responsive substance are likely sparsely coated on the cell proliferative surface formed in the patterning process, which is suitable to impart stimulus responsiveness while maintaining a patterning effect. In addition, when the layer thickness is 1 nm or more, this is suitable because it is possible to produce a cell culture substrate that can impart sufficient stimulus responsiveness and rapidly perform a spheroid formation process.

Regarding the method of coating the stimulus-responsive substance, a method of coating a stimulus-responsive substance to a substrate by a chemical bond and forming a layer, and a method of coating and forming a layer by a physical interaction can be used alone or in combination. That is, regarding a method by chemical bonding, UV emission, electron beam emission, gamma ray emission, a plasma treatment, a corona treatment, and the like can be used. In addition, when the stimulus-responsive polymer and the substrate have an appropriate reactive functional group, organic reactions that are generally used such as a radical reaction, an anion reaction, and a cation reaction can be used. Regarding a method according to a physical interaction, generally known various methods such as coating, brush coating, dip coating, spin coating, bar coating, flow coating, spray coating, roll coating, air knife coating, blade coating, gravure coating, micro gravure coating, and slot die coating, in which a matrix having favorable compatibility with a stimulus-responsive polymer and favorable coatability is used as a medium can be used.

Regarding the method of coating the stimulus-responsive substance, coating a stimulus-responsive substance to the entire surface of the cell culture substrate is preferable. If a stimulus-responsive substance is coated using an application method generally used without performing patterning when the stimulus-responsive substance is coated, it is possible to improve mass productivity of the cell culture substrate. In addition, when a stimulus-responsive substance is coated on the entire surface of the cell culture substrate, stimulus responsiveness is imparted to the region (A), and a stimulus-responsive substance is also coated on the region (B). When a stimulus-responsive substance is coated on the region (B), it is possible to reduce cell adhesion of the region (B). Therefore, when a substrate having cell adhesion but not having cell proliferation properties is used as the substrate, the region (B) has cell adhesion if only the patterning process is performed, but when a stimulus-responsive substance is also coated on the region (B), this is preferable because the region (B) can become a region having no cell adhesion, and spheroids having a uniform size and shape are easily formed. In this case, the difference of application amounts between the region (A) and the region (B) is preferably 1 μg/cm² or less, more preferably 0.8 μg/cm² or less, particularly preferably 0.6 μg/cm² or less, and most preferably 0.4 μg/cm² or less. In addition, the application amount of the region (A) and the region (B) is preferably 0.1 to 10 μg/cm², more preferably 0.5 to 7 μg/cm², particularly preferably 1 to 5 μg/cm², and most preferably 2 to 4 μg/cm².

In the method for producing a cell culture substrate of the present invention, either of the process (1) and the process (2) may be performed first. Since it is suitable to reduce the influence in the process (1), such as scratching of the layer formed of a stimulus-responsive substance on the surface, it is preferable to perform the process (2) after the process (1) is performed.

The present invention also relates to a method of producing spheroids using the cell culture substrate. In to the method, spheroids are produced according to the following processes (i) to (iii).

(i) a process of seeding a cell on the cell culture substrate.
(ii) a process of culturing the seeded cell and forming a colony of cells adhered to the cell culture substrate.
(iii) a process of separating the colony from the cell culture substrate by applying an external stimulus and forming a cell spheroid.

Hereinafter, the processes (i) to (iii) in the method of producing spheroids of the present invention will be described in detail.

The process (i) in the method for producing spheroids according to the present invention is a process in which the cell culture substrate is used and cells are seeded on the cell culture substrate. In the present invention, "seed cells" means that a culture medium in which cells are dispersed (hereinafter referred to as a "cell suspension") is applied to a cell culture substrate or injected into a cell culture substrate, and thus the cell suspension is brought into contact with the cell culture substrate. When the cell culture substrate having a cell proliferative region is used, it is possible to culture cells in the process (ii) to be described below. When the cell culture substrate has no cell proliferative region, it is not possible to culture cells in the process (ii). In addition, when the cell proliferative region additionally has a stimulus-responsive region, in the process (iii) to be described below, colonies can be separated from the cell culture substrate with an external stimulus, and spheroids can be formed. When the region has no stimulus responsiveness, in the process (iii), it is not possible to form spheroids with an external stimulus.

In the processes (i) to (iii), culturing is performed under conditions effective in maintaining cell undifferentiation. The conditions effective in maintaining the undifferentiated state are not particularly limited, and examples thereof include setting the cell density when culture starts to be within a preferable range described as the cell density during seeding below and performing culturing under an appropriate liquid culture medium. Regarding the culture medium effective in maintaining cell undifferentiation, for example, a culture medium to which at least one of insulin, transferrin, selenium, ascorbic acid, sodium bicarbonate, a basic fibroblast growth factor, a transforming growth factor β (TGFβ), CCL2, activin, and 2-mercapto methanol which are known as factors for maintaining cell undifferentiation is added can be suitably used. A culture medium containing insulin, transferrin, selenium, ascorbic acid, sodium bicarbonate, a basic fibroblast growth factor, or a transforming growth factor β (TGFβ) is more preferably used, and a culture medium to which a basic fibroblast growth factor is added is most preferably used because it is particularly suitable to maintain cell undifferentiation.

The type of the culture medium to which the basic fibroblast growth factor is added is not particularly limited, and examples thereof include commercial products DMEM (commercially available from Sigma-Aldrich Co. LLC), Ham's F12 (commercially available from Sigma-Aldrich Co. LLC), D-MEM/Ham's F12 (commercially available from Sigma-Aldrich Co. LLC), Primate ES Cell Medium (commercially available from REPROCELL), StemFit AK02N (commercially available from Ajinomoto Co., Inc.), StemFit AK03 (commercially available from Ajinomoto Co., Inc.), mTeSR1 (commercially available from STEMCELL TECHNOLOGIES), TeSR-E8 (commercially available from STEMCELL TECHNOLOGIES), ReproNaive (commercially available from REPROCELL), ReproXF (commercially available from REPROCELL), ReproFF (commercially available from REPROCELL), ReproFF2 (commercially available from REPROCELL), NutriStem (commercially available from Biological Industries), iSTEM (commercially available from Takara Bio Inc.), GS2-M (commercially available from Takara Bio Inc.), and hPSC Growth Medium DXF (commercially available from PromoCell). Primate ES Cell Medium (commercially available from REPROCELL), StemFit AK02N (commercially available from Ajinomoto Co., Inc.) or StemFit AK03 (commercially available from Ajinomoto Co., Inc.) is preferable, StemFit AK02N (commercially available from Ajinomoto Co., Inc.) or StemFit AK03 (commercially available from Ajinomoto Co., Inc.) is more preferable, and StemFit AK02N (commercially available from Ajinomoto Co., Inc.) is particularly preferable because it is suitable to maintain the undifferentiated state of cells.

In the process (i), the cell seeding method is not particularly limited, and for example, seeding can be performed by injecting a cell suspension into a cell culture substrate. The cell density during seeding is not particularly limited, and the cell density is preferably $1.0 \times 10^2$ to $1.0 \times 10^6$ cells/cm$^2$, more preferably $5.0 \times 10^2$ to $5.0 \times 10^5$ cells/cm$^2$, particularly preferably $1.0 \times 10^3$ to $2.0 \times 10^5$ cells/cm$^2$, and most preferably $1.2 \times 10^3$ to $1.0 \times 10^5$ cells/cm$^2$ so that cells can be maintained and proliferated.

Regarding the culture medium used in the process (i), a culture medium in which a Rho binding kinase inhibitor is additionally added to the culture medium to which the basic fibroblast growth factor is added is preferably used because it is suitable to maintain cell survival. In particular, when human cells are used, if the Rho binding kinase inhibitor is added when the cell density of human cells is low, it may be effective in maintaining survival of human cells. Regarding the Rho binding kinase inhibitor, for example, (R)-(+)-trans-N-(4-pyridyl)-4-(1-aminoethyl)-cyclohexanecarboxamide-2HCl·H$_2$O (Y-27632 commercially available from Wako Pure Chemical Industries, Ltd.), and 1-(5-Isoquinolinesulfonyl)homopiperazine Hydrochloride (HA1077 commercially available from Wako Pure Chemical Industries, Ltd.) can be used. The concentration of the Rho binding kinase inhibitor added to the culture medium is preferably 1 μM to 50 μM, more preferably 3 μM to 20 μM, still more preferably 5 μM to 15 μM, and most preferably 8 μM to 12 μM, which are a range effective in maintaining survival of human cells and a range that does not influence the undifferentiated state of human cells.

When the process (i) starts, immediately cells begin to adhere to the cell culture substrate.

In the process (ii) in the method for producing spheroids according to the present invention, the seeded cells are cultured. The culture temperature is preferably 30 to 42° C., more preferably 32 to 40° C., particularly preferably 36 to 38° C., and most preferably 37° C. so that it is suitable to maintain a proliferative ability, physiological activity, and functions of cells.

It is preferable to first replace a culture medium 22 to 26 hours after the process (ii) starts. It is preferable to replace the culture medium for the second time after 48 to 72 hours from the first replacement, and then to replace the culture medium every 24 to 48 hours. During this time, cells proliferate, and flat cell masses called colonies are formed. The colonies adhere to the cell culture substrate. The culture continues until the size of the colony is about the size of the region (A) and then the process proceeds to the process (iii).

In the process (iii) in the method for producing spheroids according to the present invention, an external stimulus is applied to the cell culture substrate on which cells are cultured, and at least a part of the colonies is separated from the cell culture substrate. In this case, when separation is gradually performed from the periphery of the colony, the colony is folded into a round mass, and spheroids having a uniform shape are easily formed. When the entire surface of one colony is separated from the substrate, floating spheroids can be obtained. In addition, when only the outer periphery of the colony is separated from the substrate and the central part of the colony is not separated, it is possible to form spheroids adhered to the substrate. When cooling is used as an external stimulus, in order to separate cells in a short time and reduce damage caused by cooling, the temperature during cooling is preferably 0 to 30° C., more preferably 3 to 25° C., and still more preferably 5 to 20° C. In addition, in order to reduce damage to cells, the cooling time is preferably 120 minutes or shorter, more preferably 60 minutes or shorter, particularly preferably 30 minutes or shorter, and most preferably 15 minutes or shorter.

A method of cooling a cell culture substrate in the process (iii) is not particularly limited, and for example, a method of putting a cell culture substrate into a cooling storage and cooling it, a method of placing a cell culture substrate on a cool plate and cooling it, or a method of replacing a cell culture substrate with a cooled culture medium or buffer solution and leaving it for a predetermined time can be used.

In addition, the process (iii) may include a process of generating convection in a liquid containing cultured cells in order to separate cells in a short time and reduce damage caused by an external stimulus. The method of generating convection is not particularly limited, and for example, a method of mechanically generating forced convection inside a liquid by pipetting a culture solution or a method using a pump or a stirring blade can be used.

Regarding spheroids produced by the method for producing spheroids according to the present invention, the variation in particle size of spheroids (standard deviation of particle size/average particle size) is preferably 20% or less, more preferably 15% or less, particularly preferably 10% or less, and most preferably 5% or less so that it is suitable to uniformly perform a treatment on all cells in culture after spheroid formation such as differentiation induction.

EXAMPLES

Hereinafter, the present invention will be described in detail with reference to embodiments for implementing the present invention, but these embodiments are only examples for describing the present invention, and the present invention is not limited to the following content. In addition, the embodiments can be appropriately changed and implemented within the scope of the present invention. Here, unless otherwise specified, commercially available reagents were used.

<Composition of Polymer>

The composition was determined by proton nuclear magnetic resonance spectroscopy ($^1$H-NMR) spectral analysis using a nuclear magnetic resonance measuring device (product name J NM-GSX400 commercially available from JEOL Ltd.) or carbon nuclear magnetic resonance spectroscopy ($^{13}$C-NMR) spectral analysis using a nuclear magnetic resonance measuring device (product name AVANCE III HD500 commercially available from Broker).

<Molecular Weight and Molecular Weight Distribution of Polymer>

A weight average molecular weight (Mw), a number average molecular weight (Mn) and a molecular weight distribution (Mw/Mn) were measured by gel permeation chromatography (GPC). Regarding a GPC device, HLC-8320GPC (commercially available from Tosoh Corporation)

was used, regarding columns, two of TSKgel Super AWM-H (commercially available from Tosoh Corporation) were used, the column temperature was set to 40° C., and regarding an eluent, 1,1,1,3,3,3-hexafluoro-2-isopropanol containing 10 mM sodium trifluoroacetate or N,N-dimethylformamide containing 10 mM lithium bromide was used for measurement. 1.0 mg/mL of a measurement sample was prepared and measured. For a molecular weight calibration curve, a polymethylmethacrylate having a known molecular weight (commercially available from Polymer Laboratories Ltd.) was used.

<Layer Thickness of Polymer>

The layer thickness of the polymer coated on the substrate was measured by an AFM device (SPM-9600 commercially available from Shimadzu Corporation). BL-AC40TS-C2 was used as a cantilever, the surface was scratched with tweezers, and the layer thickness of the polymer was measured by measuring the depth of the scratch.

Example 1

0.40 g (0.1 mmol) of 4-cyano-4-[(dodecylsulfanylthiocarbonyl)sulfanyl]pentanoic acid, 7.11 g (50 mmol) of n-butyl methacrylate, and 33 mg (0.2 mmol) of azobis(isobutyronitrile) were added to a test tube, and dissolved in 50 mL of 1,4-dioxane. After degassing by nitrogen bubbling for 30 minutes, the mixture was reacted at 70° C. for 24 hours. After the reaction was completed, the reaction solvent was distilled off under a reduced pressure using a rotary evaporator, and the reaction solution was concentrated. The concentrated solution was poured into 250 mL of methanol, a precipitated yellow oily substance was collected and dried under a reduced pressure, and thereby an n-butyl methacrylate polymer was obtained.

0.9 g (0.3 mmol) of the n-butyl methacrylate polymer, 8.14 g (72 mmol) of N-isopropylacrylamide, and 5 mg (0.03 mmol) of azobisisobutyronitrile were added to a test tube, and dissolved in 15 mL of 1,4-dioxane. After degassing by nitrogen bubbling for 30 minutes, the mixture was reacted at 65° C. for 17 hours. After the reaction was completed, the reaction solvent was diluted with acetone and poured into 500 mL of hexane, and a precipitated solid was collected and dried under a reduced pressure. In addition, the dried precipitated solid was dissolved in acetone again and poured into 500 mL of pure water, a precipitated solid was collected and dried under a reduced pressure, and thereby a diblock copolymer of N-isopropylacrylamide and n-butyl methacrylate was obtained.

A dish having a diameter of 10 cm and having no cell proliferation properties (material: polystyrene commercially available from As One Corporation) was covered with a metal mask having a plurality of circular holes with a diameter of 0.3 mm, a plasma treatment (under a gas pressure of 20 Pa, a conduction current of 20 mA, for an emission time of 10 seconds) was performed on the metal mask using a plasma emission device (product name plasma ion bombarder PIB-20, commercially available from Vacuum Device), and thus patterning for forming cell proliferative regions was performed. The block copolymer was dissolved in ethanol to prepare a 0.6 wt % solution, and the solution was spin-coated on the surface of the patterned substrate at 2,000 rpm for 60 seconds. Drying was performed at room temperature for 1 hour to produce a substrate coated with the block copolymer.

Here, the proportion of constituent units of the block copolymer was 4 wt % for n-butyl methacrylate and 96 wt % for N-isopropylacrylamide, and the molecular weight Mn was 77,000. The layer thickness of the block copolymer coated on the polystyrene dish was 25 nm.

0.2 mL/cm$^2$ of a culture medium StemFit AK02N (commercially available from Ajinomoto Co., Inc.) was added to the patterned substrate coated on the block copolymer, and 1,300 human iPS cell 201B7 strains/cm$^2$ were additionally added, and an iMatrix-511 solution (commercially available from Nippi. Inc.) was added at a concentration of 2.5 μL/mL. The culture was performed under an environment of 37° C. and a CO$_2$ concentration of 5%. In addition, until 24 hours after seeding of cells, Y-27632 (commercially available from Wako Pure Chemical Industries, Ltd.) (concentration of 10 μM) was added to the culture medium.

24 hours, 96 hours, and 144 hours after seeding of the cells, the conditions of the cells were observed under a phase-contrast microscope, and in all cases, cell adhesion and proliferation along the patterning shape were confirmed, and the culture medium was replaced with a new medium. After the culture medium was replaced 144 hours after seeding of the cells, the substrate was cooled at room temperature for 20 minutes, and the cells were observed under the phase-contrast microscope again. It was observed that the colonies were separated from the surroundings as cooling was performed, and spheroids were formed on the substrate. In addition, when the side surface of the substrate was tapped with hand, the spheroids were separated from the substrate, and spherical spheroids having a uniform size were collected.

Example 2

A cell culture substrate was produced in the same manner as in Example 1 except that a mask having a plurality of rectangular holes of 0.5 mmx1 mm was used in place of the metal mask in Example 1.

Cell culture was performed in the same manner as in Example 1, and 24 hours, 96 hours, and 144 hours after seeding of the cells, the conditions of cells were observed under a phase-contrast microscope, and in all cases, cell adhesion and proliferation along the patterning shape were confirmed, and the culture medium was replaced with a new medium. After the culture medium was replaced 144 hours after cells were seeded, the substrate was cooled at room temperature for 20 minutes, and the side surface of the substrate was tapped with hand. Roll-shaped spheroids having a uniform size and an elongated shape were collected.

Example 3

A cell culture substrate was produced in the same manner as in Example 1 except that a mask having a plurality of circular holes with a diameter of 0.5 mm was used in place of the metal mask in Example 1.

Cell culture was performed in the same manner as in Example 1, and 24 hours, 96 hours, and 144 hours after seeding of the cells, the conditions of cells were observed under a phase-contrast microscope, and in all cases, cell adhesion and proliferation along the patterning shape were confirmed, and the culture medium was replaced with a new medium. After the culture medium was replaced 144 hours after cells were seeded, the substrate was cooled at room temperature for 20 minutes and the cells were cultured again at 37° C. for 1 hour. The colonies were separated from the surroundings as cooling was performed, spheroids were formed, and spheroids adhered to the substrate were obtained.

Example 4

A cell culture substrate was produced in the same manner as in Example 1 except that a mask having a plurality of circular holes with a diameter of 0.2 mm was used in place of the metal mask in Example 1, and a VUV aligner (product name, commercially available from Ushio Inc.) was used in place of the plasma ion bombarder PIB-20.

Cell culture was performed in the same manner as in Example 1, and 24 hours, 96 hours, and 144 hours after seeding of the cells, the conditions of cells were observed under a phase-contrast microscope, and in all cases, cell adhesion and proliferation along the patterning shape were confirmed, and the culture medium was replaced with a new medium. After the culture medium was replaced 144 hours after cells were seeded, the substrate was cooled at room temperature for 20 minutes, and the side surface of the substrate was tapped with hand. Spherical spheroids having a uniform size were collected. The particle size of the collected spheroids was measured and the variation in the particle size (standard deviation of particle size/average particle size) was determined to be 6.6%, which was a small variation.

Example 5

A cell culture substrate was produced in the same manner as in Example 1 except that a mask having a plurality of circular holes with a diameter of 0.5 mm was used in place of the metal mask in Example 1 and a VUV aligner (product name, commercially available from Ushio Inc.) was used in place of the plasma ion bombarder PIB-20.

Cell culture was performed in the same manner as in Example 1, and 24 hours, 96 hours, and 144 hours after seeding of the cells, the conditions of cells were observed under a phase-contrast microscope, and in all cases, cell adhesion and proliferation along the patterning shape were confirmed, and the culture medium was replaced with a new medium. After the culture medium was replaced 144 hours after cells were seeded, the substrate was cooled at room temperature for 20 minutes, the side surface of the substrate was tapped with hand, cells were separated, and then additionally cultured for 1 day. Spherical spheroids having a uniform size were collected. The particle size of the collected spheroids was measured and the variation in the particle size (standard deviation of particle size/average particle size) was determined to be 14.2%, which was a small variation.

Example 6

A surface protective film (E-MASK commercially available from Nitto Denko Corporation) having a plurality of circular holes with a diameter of 0.2 mm formed by laser processing was used in place of the metal mask in Example 1, the surface protective film was attached to the substrate, a plasma treatment was performed and then the surface protective film was then separated. Then, the block copolymer was coated in the same manner as in Example 1, and a cell culture substrate was produced.

Cell culture was performed in the same manner as in Example 1, and 24 hours, 96 hours, and 144 hours after seeding of the cells, the conditions of cells were observed under a phase-contrast microscope, and in all cases, cell adhesion and proliferation along the patterning shape were confirmed, and the culture medium was replaced with a new medium. After the culture medium was replaced 144 hours after cells were seeded, the substrate was cooled at room temperature for 20 minutes, and the side surface of the substrate was tapped with hand. Spherical spheroids having a uniform size were collected. The particle size of the collected spheroids was measured and the variation in the particle size (standard deviation of particle size/average particle size) was determined to be 4.2%, which was a small variation.

Example 7

A cell culture substrate was produced in the same manner as in Example 1 except that a mask having a plurality of circular holes with a diameter of 0.2 mm was used in place of the metal mask in Example 1.

The atomic force microscopic image of the produced cell culture substrate was measured, and the region (A) had a region (A2) having a large amount of N-isopropylacrylamide polymers and a diameter of about 90 nm and other regions. In addition, the region (B) also had a region (B2) having a large amount of N-isopropylacrylamide polymers and a diameter of about 90 nm and other regions.

Cell culture was performed in the same manner as in Example 1, and 24 hours, 96 hours, and 144 hours after seeding of the cells, the conditions of cells were observed under a phase-contrast microscope, and in all cases, cell adhesion and proliferation along the patterning shape were confirmed, and the culture medium was replaced with a new medium. After the culture medium was replaced 144 hours after cells were seeded, the substrate was cooled at room temperature for 20 minutes, and the side surface of the substrate was tapped with hand. Spherical spheroids having a uniform size were collected. The particle size of the collected spheroids was measured and the variation in the particle size (standard deviation of particle size/average particle size) was determined to be 4.5%, which was a small variation.

Example 8

A mask having a plurality of circular holes with a diameter of 0.2 mm was used in place of the metal mask in Example 1, and the block copolymer was synthesized and coated by the following method.

0.40 g (0.1 mmol) of 4-cyano-4-[(dodecylsulfanylthiocarbonyl)sulfanyl]pentanoic acid, 7.11 g (50 mmol) of n-butyl methacrylate, and 33 mg (0.2 mmol) of azobis(isobutyronitrile) were added to a test tube, and dissolved in 50 mL of 1,4-dioxane. After degassing by nitrogen bubbling for 30 minutes, the mixture was reacted at 70° C. for 24 hours. After the reaction was completed, the reaction solvent was distilled off under a reduced pressure using a rotary evaporator, and the reaction solution was concentrated. The concentrated solution was poured into 250 mL of methanol, a precipitated yellow oily substance was collected and dried under a reduced pressure, and thereby an n-butyl methacrylate polymer was obtained.

0.9 g (0.3 mmol) of the n-butyl methacrylate polymer, 0.26 g (2.4 mmol) of N-isopropylacrylamide and 5 mg (0.03 mmol) of azobisisobutyronitrile were added to a test tube and dissolved in 15 mL of 1,4-dioxane. After degassing by nitrogen bubbling for 30 minutes, the mixture was reacted at 65° C. for 17 hours. After the reaction was completed, the reaction solvent was diluted with acetone and poured into 500 mL of hexane, and a precipitated solid was collected and dried under a reduced pressure. In addition, the dried precipitated solid was dissolved in acetone again and poured into 500 mL of pure water, a precipitated solid was collected and dried under a reduced pressure, and thereby copolymer of N-isopropylacrylamide and n-butyl methacrylate was obtained.

A dish having a diameter of 10 cm and having no cell proliferation properties (material: polystyrene commercially available from As One Corporation) was covered with a metal mask having a plurality of circular holes with a diameter of 0.2 mm, a plasma treatment (under a gas pressure of 20 Pa, a conduction current of 20 mA, for an emission time of 10 seconds) was performed on the metal mask using a plasma emission device (product name plasma ion bombarder PIB-20 commercially available from Vacuum Device), and thus patterning for forming a cell proliferative region was performed. The block copolymer was dissolved in ethanol to prepare a 1 wt % solution, and the solution was spin-coated on the surface of the patterned substrate at 2,000 rpm for 60 seconds. After immersion in pure water for 1 hour, drying was performed at room temperature for 24 hours to produce a substrate coated with the block copolymer.

Here, the proportion of constituent units of the block copolymer was 50 wt % for n-butyl methacrylate and 50 wt % for N-isopropylacrylamide, and the molecular weight Mn was 6,000. The layer thickness of the block copolymer coated on the polystyrene dish was 50 nm.

The atomic force microscopic image of the produced cell culture substrate was measured, and it was confirmed that the inside of the region (A) and the region (B) was uniform.

Cell culture was performed in the same manner as in Example 1, and 24 hours, 96 hours, and 144 hours after seeing of the cells, the conditions of cells were observed under a phase-contrast microscope, and in all cases, cell adhesion and proliferation along the patterning shape were confirmed, and the culture medium was replaced with a new medium. After the culture medium was replaced 144 hours after cells were seeded, the substrate was cooled at room temperature for 20 minutes, the side surface of the substrate was tapped with hand, but cells were not separated. Therefore, separation was performed by performing pipetting 20 times. Roll-shaped spheroids having a uniform size and an elongated shape were collected. The particle size of the collected spheroids was measured and the variation in the particle size (standard deviation of particle size/average particle size) was determined to be 14.6%, and although the variation was small, it was larger than the variation in Example 7.

Comparative Example 1

A cell culture substrate was produced in the same manner as in Example 1 except that no plasma treatment was performed in Example 1. Since there was no cell proliferative region, iPS cells died 24 hours after seeding, and no spheroids were formed.

Comparative Example 2

A cell culture substrate was produced in the same manner as in Example 1 except that no block copolymer was coated in Example 1. Since there was no stimulus-responsive region, colonies were not separated from the substrate, and no spheroids were collected. In addition, the shape of the colonies was also non-uniform.

Comparative Example 3

A cell culture substrate was produced in the same manner as in Example 1 except that no patterning was performed in Example 1, and a plasma treatment was performed on all regions of the substrate. The size and shape of the colonies were non-uniform. The particle size of the collected spheroids was measured and the variation in the particle size (standard deviation of particle size/average particle size) was determined to be 36.5%, which was a large variation.

Comparative Example 4

A cell culture substrate was produced in the same manner as in Example 1 except that a metal mask having a plurality of circular holes with a diameter of 4 mm was used in place of the metal mask in Example 1. The size and shape of the colonies were non-uniform. The particle size of the collected spheroids was measured and the variation in the particle size (standard deviation of particle size/average particle size) was determined to be 31.1%, which was a large variation.

Comparative Example 5

Using a commercially available cell culture container for spheroid formation (product name EZSPHERE commercially available from AGC Techno Glass Co., Ltd.) having irregularities shape on the surface and also having a cell-non-adhesive surface, cells were seeded in the same manner as in Example 1, and spheroids were formed by suspension culture. Although the formed spheroids were generally spherical, plurality of aggregates in which a plurality of spheroids were aggregated were observed. The particle size of the collected spheroids was measured and the variation in the particle size (standard deviation of particle size/average particle size) was determined to be 22.3%, which was a large variation.

Reference Example

The zeta potential in the region (A) and the region (B) in Example 1 was measured by the following method. A plasma treatment (under a gas pressure of 20 Pa, a conduction current of 20 mA, for an emission time of 10 seconds) was performed on the entire surface of a dish having a diameter of 10 cm and having no cell proliferation properties using a plasma emission device (product name plasma ion bombarder PIB-20 commercially available from Vacuum Device), and thus the entire surface of the substrate was plasma-treated. The plasma-treated substrate and a substrate on which the plasma treatment was not performed were coated with the block copolymer in the same manner as in Example 1, and thus a sample in which the entire surface of the substrate was the region (A) in Example 1 and a sample in which the entire surface of the substrate was the region (B) in Example 1 were produced. The zeta potential of these substrates were measured (SurPASS commercially available from Anton Paar was used), and the zeta potential of the region (B) was a value 8 mV larger than that of the region (A).

TABLE 1

| | Configuration of cell culture substrate | | | | | | | Evaluation of cell culture | | |
| | Region (A) | | | | | Region (B) | | | Spheroid shape | |
| Item | Configuration | Shape | Aspect ratio | Area mm² | Regions (A1) and (A2) | Configuration | Regions (B1) and (B2) | Colony shape | Spheroid shape | Variation in particle size (%) |
|---|---|---|---|---|---|---|---|---|---|---|
| Example 1 | Region having cell proliferation properties and stimulus responsiveness | Circle | 1 | 0.07 | — | Region having no cell proliferation properties | — | Circular | Spherical (suspension) | — |
| Example 2 | Region having cell proliferation properties and stimulus responsiveness | Rectangle | 2 | 0.5 | — | Region having no cell proliferation properties | — | Rectangular | Roll shape (suspension) | — |
| Example 3 | Region having cell proliferation properties and stimulus responsiveness | Circle | 1 | 0.2 | — | Region having no cell proliferation properties | — | Circular | Spherical (adhesion) | — |
| Example 4 | Region having cell proliferation properties and stimulus responsiveness | Circle | 1 | 0.03 | — | Region having no cell proliferation properties | — | Circular | Spherical (suspension) | 6.6 |
| Example 5 | Region having cell proliferation properties and stimulus responsiveness | Circle | 1 | 0.2 | — | Region having no cell proliferation properties | — | Circular | Spherical (suspension) | 14.2 |
| Example 6 | Region having cell proliferation properties and stimulus responsiveness | Circle | 1 | 0.03 | — | Region having no cell proliferation properties | — | Circular | Spherical (suspension) | 4.2 |
| Example 7 | Region having cell proliferation properties and stimulus responsiveness | Circle | 1 | 0.03 | With | Region having no cell proliferation properties | With | Circular | Spherical (suspension) | 4.5 |
| Example 8 | Region having cell proliferation properties and stimulus responsiveness | Circle | 1 | 0.03 | Without | Region having no cell proliferation properties | Without | Circular | Spherical (suspension) | 14.6 |
| Comparative Example 1 | Region having cell proliferation properties and stimulus responsiveness | Circle | 1 | 0.07 | — | Region having no cell proliferation properties | — | Cells died | — | — |
| Comparative Example 2 | Region having cell proliferation properties (without stimulus responsiveness) | Circle | 1 | 0.07 | — | Region having no cell proliferation properties | — | Non-uniform shape | x | — |
| Comparative Example 3 | Region having cell proliferation properties and stimulus responsiveness | Entire surface of substrate | | | — | Without region (B) | — | Non-uniform shape | Non-uniform shape | 31.1 |
| Comparative Example 4 | Region having cell proliferation properties and stimulus responsiveness | Circle | 1 | 12.5 | — | Region having no cell proliferation properties | — | Non-uniform shape | Non-uniform shape | 36.5 |
| Comparative Example 5 | | | | — | | | | — | Spherical (suspension) | 22.3 |

While the present invention has been described in detail with reference to specific embodiments, it will be apparent to those skilled in the art that various changes and modifications can be made without departing from the sprit and scope of the present invention.

The entire contents of the specification, claims, drawings, and abstract of Japanese Patent Application No. 2018-194841, filed Oct. 16, 2018, are cited herein and incorporated as the disclosure of the present invention.

REFERENCE SIGNS LIST

A Region (A)
B Region (B)

1 Substrate
2 Stimulus-responsive polymer
10 Cell culture substrate
20 Cell
21 Colony
22 Spheroid

The invention claimed is:

1. A cell culture substrate comprising:

a substrate, and a stimulus-responsive polymer uniformly coated on the entire surface of the substrate, wherein the stimulus-responsive polymer is a block copolymer having a water-insoluble block segment and a stimulus-responsive block segment, wherein the cell culture substrate comprises the following two regions (A) and (B):

(A) an island-shaped region having cell proliferation properties and stimulus responsiveness and having an area of 0.001 to 5 mm$^2$; and (B) a region adjacent to the region (A) and having no cell proliferation properties, wherein the region (A) is composed of the following two regions (A1) and (A2), and the region (B) is composed of the following two regions (B1) and (B2):

(A1) cell proliferative region formed in the substrate;

(A2) a first region formed in the stimulus-responsive polymer;

(B1) substrate adhesion region formed in the substrate, in which the stimulus-responsive polymer coated on the substrate adheres to the substrate; and (B2) second region formed in the stimulus-responsive polymer, wherein the cell culture substrate having (A) the island-shaped region having cell proliferation properties and (B) the region adjacent to the region (A) and having no cell proliferation properties includes a layer containing the stimulus-responsive polymer formed on the substrate, wherein the layer thickness of the layer containing the stimulus-responsive polymer is 20 nm or more and 50 nm or less, wherein a ratio of an average roughness of the layer to a layer thickness of the layer is from 0.5 or more to 1 or less, and wherein the regions (A1) are formed by a hydrophilization treatment, which is any of a plasma treatment, a UV treatment, and a corona treatment or a combination of a plurality thereof before coating the stimulus-responsive polymer on the substrate.

2. The cell culture substrate according to claim 1, wherein the region (A) is (i) formed by dispersing a temperature-responsive region having a diameter of 10 to 500 nm in a cell proliferative region, or (ii) formed by dispersing a cell proliferative region having a diameter of 10 to 500 nm in a temperature-responsive region having no cell proliferation properties.

3. The cell culture substrate according to claim 1, wherein the stimulus-responsive polymer is a block copolymer having (i) a water-insoluble block segment and (ii) a stimulus-responsive block segment exceeding 90 wt % of the block copolymer.

4. The cell culture substrate according to claim 1, wherein the region (A) is a plasma treatment region.

5. The cell culture substrate according to claim 1, wherein the cell culture substrate is used for spheroid formation for pluripotent stem cells.

6. A method for producing the cell culture substrate according to claim 1, comprising the following processes (1) and (2):

(1) a process of forming an island-shaped region having cell proliferation properties and an area of 0.001 to 5 mm$^2$ on a surface of a substrate having no cell proliferation properties; and (2) a process of forming a layer of a stimulus-responsive substance on the surface of the substrate.

7. The method for producing the cell culture substrate according to claim 6, wherein, in the process (1), on the surface of the substrate having no cell proliferation properties, a region having cell proliferation properties is formed by any of a plasma treatment, a UV treatment, and a corona treatment or a combination of a plurality thereof.

8. The method for producing the cell culture substrate according to claim 6, wherein the substrate used in the process (1) has cell adhesion properties but has no cell proliferation properties.

9. The method for producing the cell culture substrate according to claim 7, wherein the process (1) comprises a process of attaching a surface protective film having holes with an area of 0.001 to 10 mm$^2$ to the substrate.

10. A method for producing spheroids, comprising the following processes (i) to (iii):

(i) a process of seeding a cell on the cell culture substrate according to claim 1;

(ii) a process of culturing the seeded cells and forming a colony of cells adhered to the cell culture substrate; and (iii) a process of separating at least a part of the colony from the cell culture substrate by applying an external stimulus and forming a cell spheroid.

11. The cell culture substrate according to claim 1, wherein the water-insoluble block segment is a polymer of at least one monomer selected from the group consisting of n-butyl acrylate, n-butyl methacrylate, isobutyl acrylate, isobutyl methacrylate, t-butyl acrylate, t-butyl methacrylate, n-hexyl acrylate, n-hexyl methacrylate, n-octyl acrylate, n-octyl methacrylate, n-decyl acrylate, n-decyl methacrylate, n-dodecyl acrylate, n-dodecyl methacrylate, n-tetradecyl acrylate, and n-tetradecyl methacrylate.

* * * * *